(12) United States Patent
Yakym et al.

(10) Patent No.: US 12,236,346 B2
(45) Date of Patent: Feb. 25, 2025

(54) SYSTEMS AND METHODS FOR USING A CONVOLUTIONAL NEURAL NETWORK TO DETECT CONTAMINATION

(71) Applicant: GRAIL, LLC, Menlo Park, CA (US)

(72) Inventors: Christopher-James A. V. Yakym, Mountain View, CA (US); Onur Sakarya, Redwood City, CA (US)

(73) Assignee: Grail, Inc., Menlo Park, CA (US)

(*) Notice: Subject to any disclaimer, the term of this patent is extended or adjusted under 35 U.S.C. 154(b) by 820 days.

(21) Appl. No.: 17/489,458

(22) Filed: Sep. 29, 2021

(65) Prior Publication Data

US 2022/0101135 A1 Mar. 31, 2022

Related U.S. Application Data

(60) Provisional application No. 63/085,369, filed on Sep. 30, 2020.

(51) Int. Cl.
*G06N 3/08* (2023.01)
*G06F 18/214* (2023.01)
(Continued)

(52) U.S. Cl.
CPC ............ *G06N 3/08* (2013.01); *G06F 18/2148* (2023.01); *G16B 20/20* (2019.02); *G16B 30/20* (2019.02)

(58) Field of Classification Search
CPC ...................................................... G06N 3/08
(Continued)

(56) References Cited

U.S. PATENT DOCUMENTS

| 10,496,884 | B1* | 12/2019 | Nguyen | ............... | G06V 30/413 |
| 2014/0332994 | A1* | 11/2014 | Danes | .................. | G01N 23/223 |
| | | | | | 264/40.1 |

(Continued)

FOREIGN PATENT DOCUMENTS

| WO | WO 2018/081130 A1 | 5/2018 |
| WO | WO 2019/178289 A1 | 9/2019 |
| WO | WO 2020/132148 A1 | 6/2020 |

OTHER PUBLICATIONS

Klein, E. et al., "Development of a comprehensive cell-free DNA (cfDNA) assay for early detection of multiple tumor types: The Circulating Cell-free Genome Atlas (CCGA) study" 2018 ASCO Annual Meeting, Meeting Abstract, Jun. 2018, pp. 1.

(Continued)

*Primary Examiner* — Reza Nabi
(74) *Attorney, Agent, or Firm* — Fenwick & West LLP

(57) ABSTRACT

A method for training a convolutional neural net for contamination analysis is provided. A training dataset is obtained comprising, for each respective training subject in a plurality of subjects, a variant allele frequency of each respective single nucleotide variant in a respective plurality of single nucleotide variants, and a respective contamination indication. First and second subsets of the plurality of training subjects have first and second contamination indication values, respectively. A corresponding first channel comprising a first plurality of parameters that include a respective parameter for a single nucleotide variant allele frequency of each respective single nucleotide variant in a set of single nucleotide variants in a reference genome is constructed for each respective training subject. An untrained or partially trained convolutional neural net is trained using, for each respective training subject, at least the corresponding first channel of the respective training (Continued)

subject as input against the respective contamination indication.

20 Claims, 16 Drawing Sheets

(51) Int. Cl.
*G16B 20/20* (2019.01)
*G16B 30/20* (2019.01)

(58) Field of Classification Search
USPC .......................................................... 706/25
See application file for complete search history.

(56) References Cited

U.S. PATENT DOCUMENTS

| | | | |
|---|---|---|---|
| 2018/0237838 A1* | 8/2018 | Sakarya | C12Q 1/6827 |
| 2018/0237863 A1* | 8/2018 | Namsaraev | G16B 20/10 |
| 2018/0373832 A1* | 12/2018 | Sakarya | G16B 5/20 |
| 2019/0287649 A1 | 9/2019 | Filippova et al. | |
| 2019/0287652 A1 | 9/2019 | Gross et al. | |
| 2020/0003440 A1* | 1/2020 | Kim | F24F 11/52 |
| 2020/0013024 A1* | 1/2020 | Armstrong | G06Q 10/0631 |
| 2020/0134461 A1* | 4/2020 | Chai | G06N 3/084 |
| 2020/0279368 A1* | 9/2020 | Tada | A61B 1/00016 |
| 2020/0303078 A1* | 9/2020 | Mayhew | G06N 20/10 |
| 2020/0340064 A1* | 10/2020 | Gross | G16B 40/00 |
| 2020/0385813 A1 | 12/2020 | Venn | |
| 2021/0104297 A1 | 4/2021 | Venn et al. | |
| 2021/0158308 A1* | 5/2021 | Armstrong | G06Q 10/30 |
| 2021/0187732 A1* | 6/2021 | Chae | B25J 9/1653 |
| 2021/0292845 A1 | 9/2021 | Melton et al. | |
| 2021/0299706 A1* | 9/2021 | Filler | B07C 5/3416 |
| 2021/0327534 A1* | 10/2021 | Nicula | G16H 50/20 |
| 2022/0053005 A1* | 2/2022 | Liu | G06F 18/22 |
| 2022/0101135 A1* | 3/2022 | Yakym | G06N 3/08 |
| 2023/0093535 A1* | 3/2023 | Karlík | G06T 7/11 250/492.3 |
| 2023/0296313 A1* | 9/2023 | Melhem | G05B 13/027 700/285 |
| 2024/0312561 A1* | 9/2024 | Calef | G16B 20/20 |
| 2024/0312564 A1* | 9/2024 | Nohzadeh-Malakshah | G16B 40/20 |
| 2024/0410807 A1* | 12/2024 | Mareuge | G01N 21/94 |
| 2024/0412821 A1* | 12/2024 | Sakarya | G06N 20/00 |

OTHER PUBLICATIONS

Liu, M.C. et al., "Genome-wide cell-free DNA (cfDNA) methylation signatures and effect on tissue of origin (TOO) performance" 2019 ASCO Annual Meeting, Meeting Abstract, Jun. 2019, pp. 1.
PCT International Search Report and Written Opinion, PCT Application No. PCT/US2021/052709, Jan. 28, 2022, 20 pages.

* cited by examiner

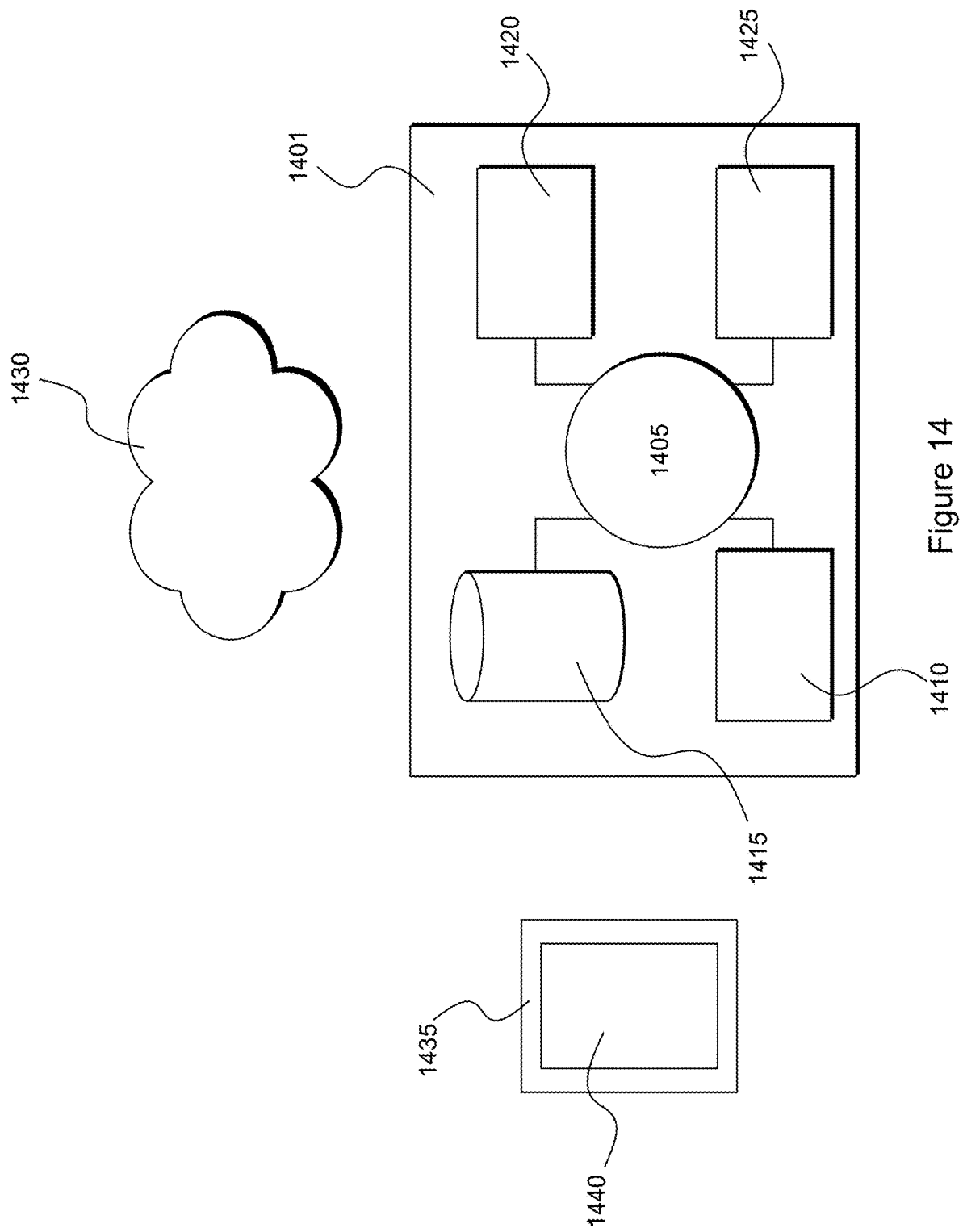

SYSTEMS AND METHODS FOR USING A CONVOLUTIONAL NEURAL NETWORK TO DETECT CONTAMINATION

CROSS REFERENCE TO RELATED APPLICATION

This application claims priority to U.S. Provisional Patent Application No. 63/085,369 entitled "System and Methods for Using a Convolutional Neural Network to Detect Contamination," filed Sep. 30, 2020, which is hereby incorporated by reference.

TECHNICAL FILED

This specification describes using a convolutional neural net (CNN) to determine whether a biological sample (e.g., cell-free nucleic acids) from a test subject is contaminated.

BACKGROUND

The increasing knowledge of the molecular basis for cancer and the rapid development of next-generation sequencing techniques are advancing the study of early molecular alterations involved in cancer development in body fluids. Large scale sequencing technologies, such as next-generation sequencing (NGS), have afforded the opportunity to achieve sequencing at costs that are less than one U.S. dollar per million bases, and in fact costs of less than ten U.S. cents per million bases have been realized. Specific genetic and epigenetic alterations associated with such cancer development are found in plasma, serum, and urine cell-free DNA (cfDNA). Such alterations could potentially be used as diagnostic biomarkers for several classes of cancers.

Cell-free DNA (cfDNA) can be found in serum, plasma, urine, and other body fluids representing a "liquid biopsy," which is a circulating picture of a specific disease. This represents a potential, non-invasive method of screening for a variety of cancers. The amount of circulating cfDNA in serum and plasma seems to be significantly higher in patients with tumors than in healthy controls, especially in those with advanced-stage tumors than in early-stage tumors. The variability of the amount of circulating cfDNA is higher in cancer patients than in healthy individuals, and the amount of circulating cfDNA is influenced by several physiological and pathological conditions, including proinflammatory diseases.

Methylation status and other epigenetic modifications can be correlated with the presence of some disease conditions such as cancer. And specific patterns of methylation have been determined to be associated with particular cancer conditions. The methylation patterns can be observed even in cell-free DNA.

SUMMARY

Given the promise of indicated such as circulating cfDNA, as well as other forms of genotypic data, as diagnostic indicators, ways of assessing the quality of such data are needed in the art to enable accurate diagnostics. The present disclosure addresses the ways of assessing the quality of genomic data by providing robust techniques for contamination detection of biological samples obtained from a subject using nucleic acid data. Moreover, the combination of transfer learning and image analysis used in some embodiments of the present disclosure provides additional diagnostic power beyond previous contamination identification methods.

Technical solutions (e.g., computing systems, methods, and non-transitory computer-readable storage mediums) for addressing the above-identified problems with analyzing datasets are provided in the present disclosure.

The following presents a summary of the invention in order to provide a basic understanding of some of the aspects of the invention. This summary is not an extensive overview of the invention. It is not intended to identify key/critical elements of the invention or to delineate the scope of the invention. Its purpose is to present some of the concepts of the invention in a simplified form as a prelude to the more detailed description that is presented later.

One aspect of the present disclosure provides a method of training a convolutional neural net for contamination analysis. In some embodiments, the method comprises, at a computer system having one or more processors, and memory storing one or more programs for execution by the one or more processors, obtaining, in electronic format, a training dataset. In some embodiments, the training dataset comprises, for each respective training subject in a plurality of training subjects: a corresponding variant allele frequency of each respective single nucleotide variant in a respective plurality of single nucleotide variants, and a respective contamination indication. In some embodiments, each variant allele frequency is determined by sequencing of one or more nucleic acids in a respective biological sample obtained from the respective training subject. At least a first subset of the plurality of training subjects has a first contamination indication value and a second subset of the plurality of training subjects has a second contamination indication value, where the second contamination indication value is other than the first contamination indication value. The method further comprises constructing, for each respective training subject in the plurality of training subjects, a corresponding first channel comprising a corresponding set of single nucleotide variants in a reference genome, each respective single nucleotide variant corresponding to an independent location in the reference genome. The respective first channel comprises a first plurality of parameters. The first plurality of parameters includes a respective parameter for a single nucleotide variant allele frequency of each respective single nucleotide variant in the set of single nucleotide variants. The method further comprises training an untrained or partially trained convolutional neural net using, for each respective training subject in the plurality of training subjects, at least the corresponding first channel of the respective training subject, as input to the untrained or partially trained convolutional neural net, against the respective contamination indication.

In some embodiments, the method further comprising pre-training the untrained or partially trained convolutional neural net, where the pre-training comprises: obtaining, in electronic format, a pre-training dataset, where the pre-training dataset comprises, for each respective pre-training object in a plurality of pre-training objects: a corresponding image (e.g., an RGB color image), and a respective pre-training label; and training the untrained or partially trained convolutional neural net using, for each respective pre-training object in the plurality of pre-training objects, at least the corresponding image of the respective pre-training object as input to the untrained or partially trained convolutional neural net against the respective pre-training label.

In some embodiments, training the untrained or partially trained convolutional neural net includes modifying or replacing an initial classification layer of the untrained or partially trained convolutional neural net with a contamination analysis classification layer (e.g., a contaminated versus non-contaminated binary classification layer).

In some embodiments, the method further comprising determining a contamination status for a biological sample of a test subject of a species, where determining the contamination status comprises obtaining, in electronic format, a test subject dataset. In some embodiments, the test subject dataset comprises a corresponding variant allele frequency of each respective single nucleotide variant in a subject plurality of single nucleotide variants, where each variant allele frequency is determined by sequencing of one or more nucleic acids in the biological sample obtained from the test subject. In some embodiments the method further comprises constructing a first channel of the test subject (e.g., represented as an image) comprising a corresponding set of single nucleotide variants in the reference genome, each respective single nucleotide variant corresponding to an independent location in the reference genome, where the first channel of the test subject comprises a first plurality of parameters. In some embodiments the first plurality of parameters includes a respective parameter for a single nucleotide variant allele frequency of each respective single nucleotide variant in the set of single nucleotide variants. In some embodiments, the method further comprises applying the first channel of the test subject to the trained computational neural net, thereby obtaining a test contamination indication for the biological sample of the test subject.

In some embodiments, the test subject sample is determined to be contaminated when a test contamination indication satisfies a contamination threshold. In some embodiments, the method further comprises determining a contamination confidence value for the test contamination indication.

In some embodiments, the corresponding set of single-nucleotide variants in the first channel are ordered in accordance with a respective position of each single nucleotide variant in the corresponding set of single-nucleotide variants in the reference genome. In some embodiments, each nucleic acid variant in the corresponding set of single-nucleotide variants in the first channel is fixed to a respective position along a first axis in the first channel.

In some embodiments, the first and/or second contamination indication value is selected from the set comprising 0.1%, 0.3%, 0.5%, 1%, 5%, 10%, 15%, 20%, and 25%. In some embodiments, each corresponding variant allele frequency is between 0 and 1.

In some embodiments, the training dataset comprises a plurality of subsets of training subjects (e.g., subsets of the plurality of training subjects), where each subset of training subjects has a respective contamination indication value.

In some embodiments, each subset of training subjects comprises at least 20 training subjects, at least 40 training subjects, at least 60 training subjects, at least 80 training subjects, at least 100 training subjects, at least 150 training subjects, at least 200 training subjects, at least 250 training subjects, at least 300 training subjects, at least 400 training subjects, at least 500 training subjects, at least 600 training subjects, at least 700 training subjects, at least 800 training subjects, at least 900 training subjects, or at least 1000 training subjects.

In some embodiments, the method further comprises constructing, for each respective training subject in the plurality of training subjects, a corresponding second channel that comprises a second plurality of parameters. In some embodiments, the second plurality of parameters includes a respective parameter for a single nucleotide variant depth of each respective single nucleotide variant in the set of single nucleotide variants. Thus, in such embodiments, for a given training subject for a given single nucleotide variant, a first parameter in the first plurality of parameters may encode a single nucleotide variant allele frequency of a single nucleotide variant corresponding to the first parameter while a corresponding second parameter in the second plurality of parameters may encode a sequencing depth for this single nucleotide variant. In some embodiments, each parameter in the second plurality of parameters may uniquely correspond to a parameter in the first plurality of parameters, and each parameter in the first plurality of parameters may uniquely correspond to a single nucleotide variant in the set of single nucleotide variants.

In some embodiments, the method further comprises constructing, for each respective training subject in the plurality of training subjects, a corresponding third channel that comprises a third plurality of parameters, where the third plurality of parameters includes a respective parameter for an error statistic of each respective single nucleotide variant in the set of single nucleotide variants. In some embodiments, the single nucleotide variant error statistic comprises a site specific error rate (e.g., for the particular site of the SNV). In some embodiments, the single nucleotide variant error statistic comprises a trinucleotide context error rate. Thus, in such embodiments, for a given training subject for a given single nucleotide variant, a first parameter in the first plurality of parameters may encode a single nucleotide variant allele frequency of a single nucleotide variant corresponding to the first parameter, while a corresponding second parameter in the second plurality of parameters may encode a sequencing depth for this single nucleotide variant, while a corresponding third parameter in the third plurality of parameters may encode an error statistic associated with the sequencing of this single nucleotide variant. In some embodiments, each parameter in the third plurality of parameters may uniquely correspond to a parameter in the second plurality of parameters, each parameter in the second plurality of parameters may uniquely correspond to a parameter in the first plurality of parameters, and each parameter in the first plurality of parameters may uniquely correspond to a single nucleotide variant in the set of single nucleotide variants.

In some embodiments, the method further comprises constructing, for each respective training subject in the plurality of training subjects, a corresponding fourth channel comprising a fourth plurality of parameters, where the fourth plurality of parameters includes a respective parameter indicating a loss of heterozygosity status for each respective single nucleotide variant in the set of single nucleotide variants. Thus, in such embodiments, for a given training subject for a given single nucleotide variant, a first parameter in the first plurality of parameters may encode a single nucleotide variant allele frequency of a single nucleotide variant corresponding to the first parameter, while a corresponding second parameter in the second plurality of parameters may encode a sequencing depth for this single nucleotide variant, while a corresponding third parameter in the third plurality of parameters may encode an error statistic associated with the sequencing of this single nucleotide variant, while a corresponding fourth parameter in the fourth plurality of parameters may encode a parameter indicating a loss of heterozygosity status for this single nucleotide variant. In some embodiments, each parameter in the fourth plurality of parameters may uniquely correspond to a parameter in the third plurality of parameters, each parameter in the third plurality of parameters may uniquely correspond to a parameter in the second plurality of parameters, each parameter in the second plurality of parameters may uniquely correspond to a parameter in the first plurality of parameters, and each parameter in the first plurality of parameters may uniquely correspond to a single nucleotide variant in the set of single nucleotide variants.

In some embodiments, the training dataset comprises at least 20 training subjects, at least 40 training subjects, at least 60 training subjects, at least 80 training subjects, at least 100 training subjects, at least 150 training subjects, at least 200 training subjects, at least 250 training subjects, at least 300 training subjects, at least 350 training subjects, at least 400 training subjects, at least 450 training subjects, at least 500 training subjects, at least 600 training subjects, at least 700 training subjects, at least 800 training subjects, at least 900 training subjects, at least 1000 training subjects, at least 2000 training subjects, at least 3000 training subjects, at least 4000 training subjects, at least 5000 training subjects, at least 6000 training subjects, at least 7000 training subjects, at least 8000 training subjects, at least 9000 training subjects, or at least 10,000 training subjects.

In some embodiments, the corresponding set of single nucleotide variants comprises each possible single nucleotide variant of the reference genome.

In some embodiments, for a respective training subject, the corresponding plurality of single nucleotide variants comprises each single nucleotide variant present in the respective biological sample of the respective training subject.

In some embodiments, each training subject in the plurality of training subjects is human. In some embodiments, the test subject is human. In some embodiments, the reference genome comprises a human genome.

In some embodiments, the untrained or partially trained convolutional neural net comprises at least one of: one or more convolutional layers, where each convolutional layer comprises one or more filters (e.g., kernels), a respective size (e.g., n×n, where n is a positive integer), and a respective stride, one or more pooling layers, where each pooling layer comprises a respective size and a respective stride, one or more fully connected layers, where each fully connected layer comprises a plurality of nodes, and one or more of a classifying layer and/or a hidden layer.

In some embodiments, the untrained or partially trained convolutional neural net further comprises one or more hyperparameters (e.g., one or more fixed constants that may be tuned during training). In some embodiments, the one or more hyperparameters are tuned during cross-validation.

In some embodiments, a respective hyperparameter of the one or more hyperparameters comprises a number of epochs. In some embodiments, a respective hyperparameter of the one or more hyperparameters comprises a batch size. In some embodiments, a respective hyperparameter of the one or more hyperparameters comprises a learning rate. In some embodiments, a respective hyperparameter of the one or more hyperparameters comprises momentum.

In some embodiments, the untrained or partially trained convolutional neural net uses one or more layers of a convolutional neural network that has been trained on pixelated image data (e.g., RGB pixelated images), with no requirement that the images be biologically related. Examples of such trained convolutional neural nets include, but are not limited to, LeNet, AlexNet, VGGNet 16, GoogLeNet, or ResNet. In some embodiments, the untrained or partially trained neural net comprises a multilayer neural net, a deep convolutional neural net, a visual geometry convolutional neural net, or a combination thereof. In some embodiments, the untrained or partially trained convolutional neural net uses all the layers of a convolutional neural network that has been trained on non-biological data, other than the classification layers of the convolutional neural network.

In some embodiments, the method further comprises, for each training subject in the plurality of training subjects, selecting the respective contamination indication value (e.g., randomly selected from the set of contamination indication values), and for each respective single nucleotide variant in the respective plurality of single nucleotide variants, obtaining, a respective plurality of sequence reads from the respective biological sample, and selecting a percentage of sequence reads from the training subject and a percentage of sequence reads from a reference set to determine the corresponding variant allele frequency.

In some embodiments, the reference set comprises a composite of a set of reference samples (e.g., represent an average variant allele frequency for a reference set of subjects—e.g., from a publicly available dataset of individuals).

Another aspect of the present disclosure provides a method of determining a contamination status of a test biological sample obtained from a test subject, comprising: (a) obtaining, in electronic format, one or more training subject datasets, each training subject dataset comprising a corresponding training variant allele frequency of each respective training single nucleotide variant in a plurality of training single nucleotide variants, wherein each training variant allele frequency in the plurality of training single nucleotide variants is determined by sequencing one or more nucleic acids in one or more training biological samples, and wherein the plurality of training single nucleotide variants comprise 100 or more training single nucleotide variants; (b) training a computational neural net based on the one or more training subject datasets, wherein the computational neural net comprises a pre-trained convolutional neural net and an untrained classifier; (c) obtaining, in electronic format, a test subject dataset comprising a corresponding test variant allele frequency of each respective test single nucleotide variant in a plurality of test single nucleotide variants, wherein each test variant allele frequency in the plurality of test single nucleotide variants is determined by sequencing one or more nucleic acids in the test biological sample, and wherein the plurality of test single nucleotide variants comprise 100 or more test single nucleotide variants; and (d) determining the contamination status for the test biological sample based on the trained computational neural net and the test subject dataset.

Another aspect of the present disclosure provides a method of determining a contamination status of a test biological sample obtained from a test subject, comprising: (a) obtaining, in electronic format, one or more training subject datasets, each training subject dataset comprising a corresponding training variant allele frequency of each respective training single nucleotide variant in a plurality of training single nucleotide variants; (b) training a computational neural net based on the one or more training subject datasets, wherein the computational neural net comprises a pre-trained convolutional neural net and an untrained classifier; (c) obtaining, in electronic format, a test subject dataset comprising a corresponding test variant allele frequency of each respective test single nucleotide variant in a plurality of test single nucleotide variants; and (d) determining the contamination status for the test biological sample based on the trained computational neural net and the test subject dataset.

Another aspect of the present disclosure provides a computing system, comprising one or more processors, and memory storing one or more programs to be executed by the one or more processors. The one or more programs comprise instructions of instructions for training a convolutional neural net for contamination analysis by a method. The method comprises obtaining, in electronic format, a training dataset. The training dataset comprises, for each respective training subject in a plurality of training subjects: a corresponding variant allele frequency of each respective single nucleotide variant in a respective plurality of single nucleotide variants, and a respective contamination indication. Each variant allele frequency is determined by sequencing one or more nucleic acids in a respective biological sample obtained from the respective training subject. At least a first subset of the plurality of training subjects has a first contamination indication value and a second subset of the plurality of training subjects has a second contamination indication value, where the first contamination indication value is other than the second contamination indication value. The method further comprises constructing, for each respective training subject in the plurality of training subjects, a corresponding first channel comprising a corresponding set of single nucleotide variants in a reference genome, each respective single nucleotide variant corresponding to an independent location in the reference genome. The respective first channel comprises a first plurality of parameters. The first plurality of parameters includes a respective parameter for a single nucleotide variant allele frequency of each respective single nucleotide variant in the set of single nucleotide variants. The method further comprises training an untrained or partially trained convolutional neural net using, for each respective training subject in the plurality of training subjects, at least the corresponding first channel of the respective training subject, as input to the untrained or partially trained convolutional neural net, against the respective contamination indication.

Another aspect of the present disclosure provides a computing system including the above-disclosed one or more processors and memory storing one or more programs that further comprise instructions for performing any of the above-disclosed methods alone or in combination.

Another aspect of the present disclosure provides a non-transitory computer-readable storage medium storing one or more programs for training a convolutional neural net for contamination analysis. The one or more programs are configured for execution by a computer. Moreover, the one or more programs comprise instructions for obtaining, in electronic format, a training dataset. The training dataset comprises, for each respective training subject in a plurality of training subjects: a corresponding variant allele frequency of each respective single nucleotide variant in a respective plurality of single nucleotide variants, and a respective contamination indication. Each variant allele frequency is determined by sequencing one or more nucleic acids in a respective biological sample obtained from the respective training subject. At least a first subset of the plurality of training subjects has a first contamination indication value and a second subset of the plurality of training subjects has a second contamination indication value, where the first contamination indication value is other than the second contamination indication value. The one or more programs further comprise instructions for constructing, for each respective training subject in the plurality of training subjects, a corresponding first channel comprising a corresponding set of single nucleotide variants in a reference genome, each respective single nucleotide variant corresponding to an independent location in the reference genome. The respective first channel comprises a first plurality of parameters. The first plurality of parameters includes a respective parameter for a single nucleotide variant allele frequency of each respective single nucleotide variant in the set of single nucleotide variants. The one or more programs further comprise instructions for training an untrained or partially trained convolutional neural net using, for each respective training subject in the plurality of training subjects, at least the corresponding first channel of the respective training subject, as input to the untrained or partially trained convolutional neural net, against the respective contamination indication.

Another aspect of the present disclosure provides non-transitory computer-readable storage medium comprising the above-disclosed one or more programs in which the one or more programs further comprise instructions for performing any of the above-disclosed methods alone or in combination. The one or more programs are configured for execution by a computer.

Various embodiments of systems, methods, and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIG. 14 illustrates an exemplary computer system 1401 that is programmed or otherwise configured to determine a disease condition of a test subject, according to one or more embodiments of the present disclosure

DETAILED DESCRIPTION

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions for contamination analysis of a biological sample of a test subject. A convolutional neural net can be trained to classify biological samples as contaminated or not based on image data (e.g., images such as the graphs in FIGS. 3A and 3B), thereby providing increased confidence for downstream analyses of disease detection or clinical diagnosis (e.g., of cancer) that are based on the biological sample for the test subject.

Figure 9:
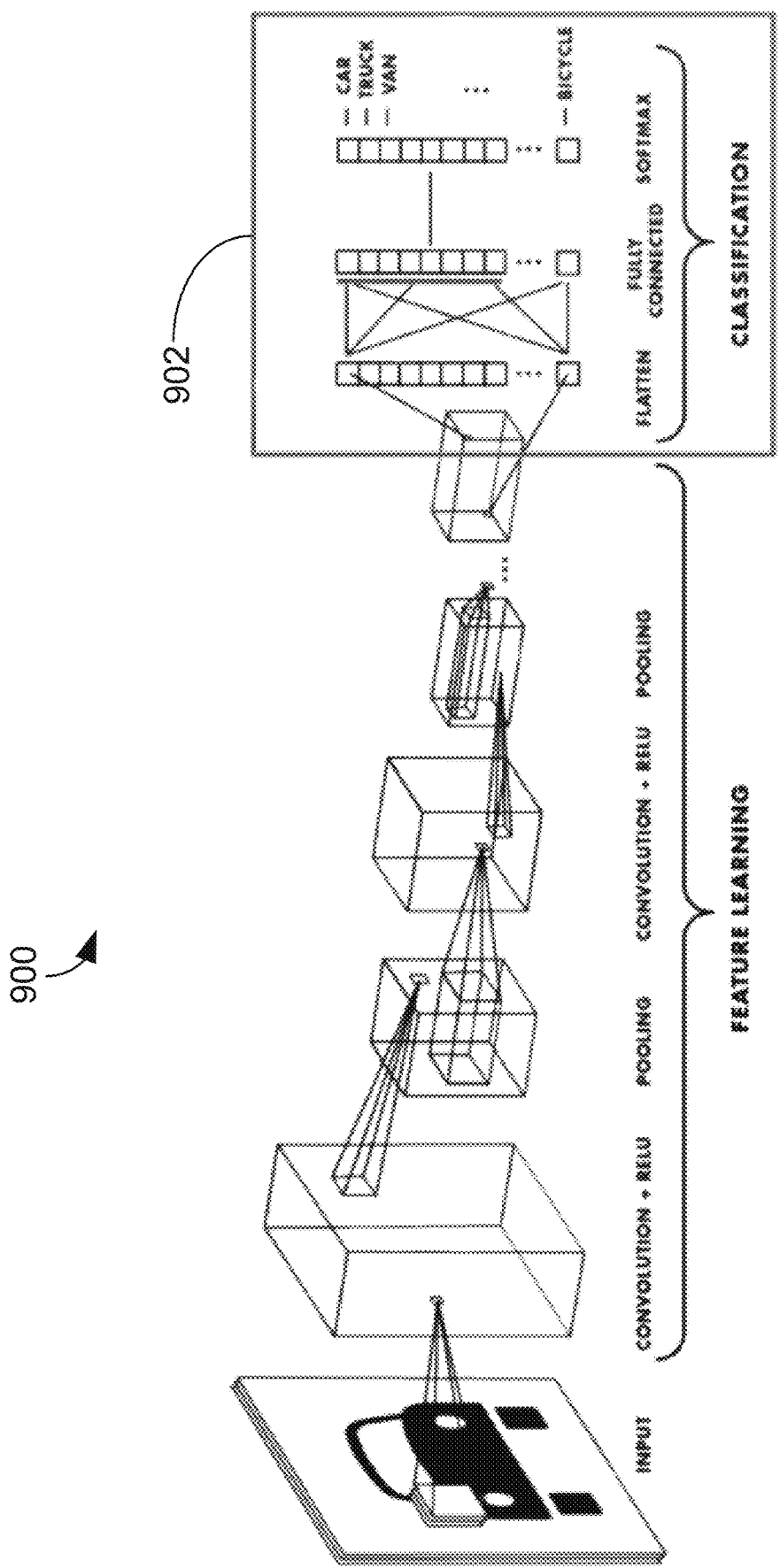
FIG. 9 illustrates a convolutional neural network trained on pixelated images, where the convolutional neural network includes multinomial classification layers in accordance with the prior art.

In some embodiments, the trained convolutional neural net can be pre-trained with non-clinical image data (e.g., non-relevant images) and transfer learning can be used to apply the pre-trained convolutional neural net to biological sample information. For instance, in some embodiments one or more classification layers, for example the layers indicated by box 902 of the pre-trained convolutional neural net 900 of FIG. 9, can be replaced with a contamination analysis classification layer. While the classification layers 902 of pre-trained convolutional neural net 900 may select from more than two classifications (e.g., car, truck, van, . . . , bicycle), the contamination analysis classification layer may output a binary classification: contaminated or not contaminated. In some alternative embodiments, rather than outputting a binary classification, the contamination analysis classification layer outputs a probability that the sample is contaminated or a probability that the sample is not contaminated. Nonlimiting examples of pre-trained convolutional neural nets that can be used include LeNet, AlexNet, VGGNet 16, GoogLeNet, and ResNet. For instance, in some embodiments the pre-trained convolutional neural net may be ResNet34 trained on a dataset of 14 million manually annotated images from over 100,000 classes. Referring to FIG. 9, in such examples of pre-trained convolutional neural nets, one or more of the classification layers 902 of the pre-trained convolutional neural net 900, which provides an option for each of the over 100,000 classes, may be replaced with the contamination analysis classification layer. In some embodiments, this contamination analysis classification layer indicates whether or not a sample is contaminated.

The biological samples can be represented as images (e.g., images of variant allele frequencies) for the purpose of contamination analysis. The methods described herein can improve contamination detection thus aiding in sample evaluability decisions (e.g., determining which samples to use for downstream analysis) during studies as well as guard against calling false positives in clinical settings (e.g., enabling more accurate disease diagnoses for patients).

Definitions

As used herein, the term "about" or "approximately" means within an acceptable error range for the particular value as determined by one of ordinary skill in the art, which depends in part on how the value is measured or determined, e.g., the limitations of the measurement system. For example, in some embodiments "about" mean within 1 or more than 1 standard deviation, per the practice in the art. In some embodiments, "about" means a range of ±20%, ±10%, ±5%, or ±1% of a given value. In some embodiments, the term "about" or "approximately" means within an order of magnitude, within 5-fold, or within 2-fold, of a value. Where particular values are described in the application and claims, unless otherwise stated the term "about" meaning within an acceptable error range for the particular value can be assumed. The term "about" can have the meaning as commonly understood by one of ordinary skill in the art. In some embodiments, the term "about" refers to ±10%. In some embodiments, the term "about" refers to ±5%.

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variant of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay can be used to detect any of the properties of nucleic acids mentioned herein. Properties of a nucleic acid molecule can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid molecule (e.g., the nucleotide position(s) at which a nucleic acid fragments). An assay or method can have a particular sensitivity and/or specificity, and their relative usefulness as a diagnostic tool can be measured using ROC-AUC statistics.

As disclosed herein, the term "biological sample" refers to any sample taken from a subject, which can reflect a biological state associated with the subject, and that includes cell-free DNA. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. A biological sample can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

As disclosed herein, the terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid molecule can be in any form useful for conducting processes herein (e.g., linear, circular, supercoiled, single-stranded, double-stranded and the like). A nucleic acid in some embodiments can be from a single chromosome or fragment thereof (e.g., a nucleic acid sample may be from one chromosome of a sample obtained from a diploid organism). In certain embodiments, nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with proteins or other molecules. Nucleic acids also include derivatives, variants and analogs of RNA or DNA synthesized, replicated or amplified from single-stranded ("sense" or "antisense," "plus" strand or "minus" strand, "forward" reading frame or "reverse" reading frame) and double-stranded polynucleotides. Deoxyribonucleotides include deoxyadenosine, deoxycytidine, deoxyguanosine, and deoxythymidine. For RNA, the base cytosine is replaced with uracil and the sugar 2' position includes a hydroxyl moiety. A nucleic acid may be prepared using a nucleic acid obtained from a subject as a template.

As disclosed herein, the terms "cell-free nucleic acid," "cell-free DNA," and "cfDNA" interchangeably refer to nucleic acid fragments that circulate in a subject's body (e.g., in a bodily fluid such as the bloodstream) and originate from one or more healthy cells and/or from one or more cancer cells. Cell-free DNA may be recovered from bodily fluids such as blood, whole blood, plasma, serum, urine, cerebrospinal fluid, fecal, saliva, sweat, sweat, tears, pleural fluid, pericardial fluid, or peritoneal fluid of a subject. Cell-free nucleic acids are used interchangeably with circulating nucleic acids. Examples of the cell-free nucleic acids include but are not limited to RNA, mitochondrial DNA, or genomic DNA.

As disclosed herein, the term "circulating tumor DNA" or "ctDNA" refers to nucleic acid fragments that originate from aberrant tissue, such as the cells of a tumor or other types of cancer, which may be released into a subject's bloodstream as a result of biological processes such as apoptosis or necrosis of dying cells or actively released by viable tumor cells.

As disclosed herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As disclosed herein, the term "regions of a reference genome," "genomic region," or "chromosomal region" refers to any portion of a reference genome, contiguous or non-contiguous. It can also be referred to, for example, as a bin, a partition, a genomic portion, a portion of a reference genome, a portion of a chromosome and the like. In some embodiments, a genomic section is based on a particular length of the genomic sequence. In some embodiments, a method can include analysis of multiple mapped sequence reads to a plurality of genomic regions. Genomic regions can be approximately the same length or the genomic sections can be different lengths. In some embodiments, genomic regions are of about equal length. In some embodiments, genomic regions of different lengths are adjusted or weighted. In some embodiments, a genomic region is about 10 kilobases (kb) to about 500 kb, about 20 kb to about 400 kb, about 30 kb to about 300 kb, about 40 kb to about 200 kb, and sometimes about 50 kb to about 100 kb. In some embodiments, a genomic region is about 100 kb to about 200 kb. A genomic region is not limited to contiguous runs of sequence. Thus, genomic regions can be made up of contiguous and/or non-contiguous sequences. A genomic region is not limited to a single chromosome. In some embodiments, a genomic region includes all or part of one chromosome or all or part of two or more chromosomes. In some embodiments, genomic regions may span one, two, or more entire chromosomes. In addition, the genomic regions may span joint or disjointed portions of multiple chromosomes.

As used herein, the term "nucleic acid fragment sequence" refers to all or a portion of a polynucleotide sequence of at least three consecutive nucleotides. In the context of sequencing nucleic acid fragments found in a biological sample, the term "nucleic acid fragment sequence" refers to the sequence of a nucleic acid molecule (e.g., a DNA fragment) that is found in the biological sample or a representation thereof (e.g., an electronic representation of the sequence). Sequencing data (e.g., raw or corrected sequence reads from whole-genome sequencing, targeted sequencing, etc.) from a unique nucleic acid fragment (e.g., a cell-free nucleic acid) are used to determine a nucleic acid fragment sequence. Such sequence reads, which in fact may be obtained from sequencing of PCR duplicates of the original nucleic acid fragment, therefore "represent" or "support" the nucleic acid fragment sequence. There may be a plurality of sequence reads that each represents or supports a particular nucleic acid fragment in a biological sample (e.g., PCR duplicates), however, there may be one nucleic acid fragment sequence for the particular nucleic acid fragment. In some embodiments, duplicate sequence reads generated for the original nucleic acid fragment are combined or removed (e.g., collapsed into a single sequence, e.g., the nucleic acid fragment sequence). Accordingly, when determining metrics relating to a population of nucleic acid fragments, in a sample, that each encompasses a particular locus (e.g., an abundance value for the locus or a metric based on a characteristic of the distribution of the fragment lengths), the nucleic acid fragment sequences for the population of nucleic acid fragments, rather than the supporting sequence reads (e.g., which may be generated from PCR duplicates of the nucleic acid fragments in the population, can be used to determine the metric. This is because, in such embodiments, one copy of the sequence is used to represent the original (e.g., unique) nucleic acid fragment (e.g., unique nucleic acid molecule). It is noted that the nucleic acid fragment sequences for a population of nucleic acid fragments may include several identical sequences, each of which represents a different original nucleic acid fragment, rather than duplicates of the same original nucleic acid fragment. In some embodiments, a cell-free nucleic acid is considered a nucleic acid fragment.

The terms "sequence reads" or "reads," used interchangeably herein, refer to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130 bp, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp.

As disclosed herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

As disclosed herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the term "methylation" refers to a modification of deoxyribonucleic acid (DNA) where a hydrogen atom on the pyrimidine ring of a cytosine base is converted to a methyl group, forming 5-methylcytosine. Methylation tends to occur at dinucleotides of cytosine and guanine referred to herein as "CpG sites". In other instances, methylation may occur at a cytosine not part of a CpG site or at another nucleotide that's not cytosine; however, these are rarer occurrences. In this present disclosure, methylation is discussed in reference to CpG sites for the sake of clarity. Anomalous cfDNA methylation can be identified as hypermethylation or hypomethylation, both of which may be indicative of cancer status. As is well known in the art, DNA methylation anomalies (compared to healthy controls) can cause different effects, which may contribute to cancer.

Various challenges arise in the identification of anomalously methylated cfDNA fragments. First, determining a subject's cfDNA to be anomalously methylated holds weight in comparison with a group of control subjects, such that if the control group is small in number, the determination loses confidence with the small control group. Additionally, among a group of control subjects' methylation status can vary which can be difficult to account for when determining a subject's cfDNA to be anomalously methylated. On another note, methylation of a cytosine at a CpG site causally influences methylation at a subsequent CpG site.

The principles described herein can be equally applicable for the detection of methylation in a non-CpG context, including non-cytosine methylation. Further, the methylation state vectors may contain elements that are generally vectors of sites where methylation has or has not occurred (even if those sites are not CpG sites specifically). With that substitution, the remainder of the processes described herein are the same, and consequently, the inventive concepts described herein are applicable to those other forms of methylation.

As disclosed herein, the term "subject," "training subject," or "test subject" refers to any living or non-living organism, including but not limited to a human (e.g., a male human, female human, fetus, pregnant female, child, or the like), a non-human animal, a plant, a bacterium, a fungus or a protist. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale, and shark. The terms "subject" and "patient" are used interchangeably herein and refer to a human or non-human animal who is known to have, or potentially has, a medical condition or disorder, such as, e.g., a cancer. In some embodiments, a subject is a male or female of any stage (e.g., a man, a woman, or a child).

A subject from whom a sample is taken, or is treated by any of the methods or compositions described herein can be of any age and can be an adult, infant or child. In some cases, the subject, e.g., patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between about 2 and about 20 years old, between about 20 and about 40 years old, or between about 40 and about 90 years old). A particular class of subjects, e.g., patients that can benefit from a method of the present disclosure is subjects, e.g., patients over the age of 40.

Another class of subjects, e.g., patients that can benefit from a method of the present disclosure is pediatric patients, who can be at higher risk of chronic heart symptoms. Furthermore, a subject, e.g., a patient from whom a sample is taken, or is treated by any of the methods or compositions described herein, can be male or female.

The term "normalize" as used herein means transforming a value or a set of values to a common frame of reference for comparison purposes. For example, when a diagnostic ctDNA level is "normalized" with a baseline ctDNA level, the diagnostic ctDNA level is compared to the baseline ctDNA level so that the amount by which the diagnostic ctDNA level differs from the baseline ctDNA level can be determined.

As used herein the term "cancer" or "tumor" refers to an abnormal mass of tissue in which the growth of the mass surpasses and is not coordinated with the growth of normal tissue. A cancer or tumor can be defined as "benign" or "malignant" depending on the following characteristics: a degree of cellular differentiation including morphology and functionality, rate of growth, local invasion and metastasis. A "benign" tumor can be well-differentiated, have characteristically slower growth than a malignant tumor and remain localized to the site of origin. In addition, in some cases, a benign tumor does not have the capacity to infiltrate, invade or metastasize to distant sites. A "malignant" tumor can be poorly differentiated (anaplasia), have characteristically rapid growth accompanied by progressive infiltration, invasion, and destruction of the surrounding tissue. Furthermore, a malignant tumor can have the capacity to metastasize to distant sites.

As used herein, the term "level of cancer" refers to whether cancer exists (e.g., presence or absence), a stage of a cancer, a size of tumor, presence or absence of metastasis, the total tumor burden of the body, and/or other measures of severity of a cancer (e.g., recurrence of cancer). The level of cancer can be a number or other indicia, such as symbols, alphabet letters, and colors. The level can be zero. The level of cancer can also include premalignant or precancerous conditions (states) associated with mutations or a number of mutations. The level of cancer can be used in various ways.

For example, screening can check if cancer is present in someone who is not known previously to have cancer. Assessment can investigate someone who has been diagnosed with cancer to monitor the progress of cancer over time, to study the effectiveness of therapies, or to determine the prognosis. In one embodiment, the prognosis can be expressed as the chance of a subject dying of cancer, or the chance of the cancer progressing after a specific duration or time, or the chance of cancer metastasizing. Detection can comprise 'screening' or can comprise checking if someone, with suggestive features of cancer (e.g., symptoms or other positive tests), has cancer.

The terms "cancer load," "tumor load," "cancer burden" and "tumor burden" are used interchangeably herein to refer to a concentration or presence of tumor-derived nucleic acids in a test sample. As such, the terms "cancer load," "tumor load," "cancer burden" and "tumor burden" are non-limiting examples of a cell source fraction in a biological sample As used herein, the term "tissue" corresponds to a group of cells that group together as a functional unit. More than one type of cell can be found in a single tissue. Different types of tissue may consist of different types of cells (e.g., hepatocytes, alveolar cells or blood cells), but also can correspond to tissue from different organisms (mother vs. fetus) or to healthy cells vs. tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

As used herein the term "untrained classifier" refers to a classifier that has not been trained on a target dataset. Moreover, the term "untrained classifier" does not exclude the possibility that transfer learning techniques are used in such training of the untrained classifier. In instances where transfer learning is used, an untrained classifier is provided with additional data over and beyond that of a primary training dataset.

The term "classification" can refer to any number(s) or other characters(s) that are associated with a particular property of a sample. For example, a "+" symbol (or the word "positive") can signify that a sample is classified as having deletions or amplifications. In another example, the term "classification" refers to an amount of tumor tissue in the subject and/or sample, a size of the tumor in the subject and/or sample, a stage of the tumor in the subject, a tumor load in the subject and/or sample, and presence of tumor metastasis in the subject. In some embodiments, the term "classification" refers to a contamination state of a biological sample. In some embodiments, the classification is binary (e.g., positive or negative) or has more levels of classification (e.g., a scale from 1 to 10 or 0 to 1). In some embodiments, the terms "cutoff" and "threshold" refer to predetermined numbers used in an operation. In one example, a cutoff size refers to a size above which fragments are excluded. In some embodiments, a threshold value is a value above or below which a particular classification applies. Either of these terms can be used in either of these contexts.

As used herein, the terms "control," "control sample," "reference," "training sample," "normal," and "normal sample" describe a sample from a subject that does not have a particular condition, or is otherwise healthy. In an example, a method as disclosed herein can be performed on a subject having a tumor, where the training sample is a sample taken from a healthy tissue of the subject. A training sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of a constitutional sample can be DNA of white blood cells obtained from the subject. For a haploid genome, there can be one nucleotide at each locus. For a diploid genome, heterozygous loci can be identified; each heterozygous locus can have two alleles, where either allele can allow a match for alignment to the locus.

Several aspects are described below with reference to example applications for illustration. Numerous specific details, relationships, and methods are set forth to provide a full understanding of the features described herein. The features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are used to implement a methodology in accordance with the features described herein.

Exemplary System Embodiments.

Figure 1A:
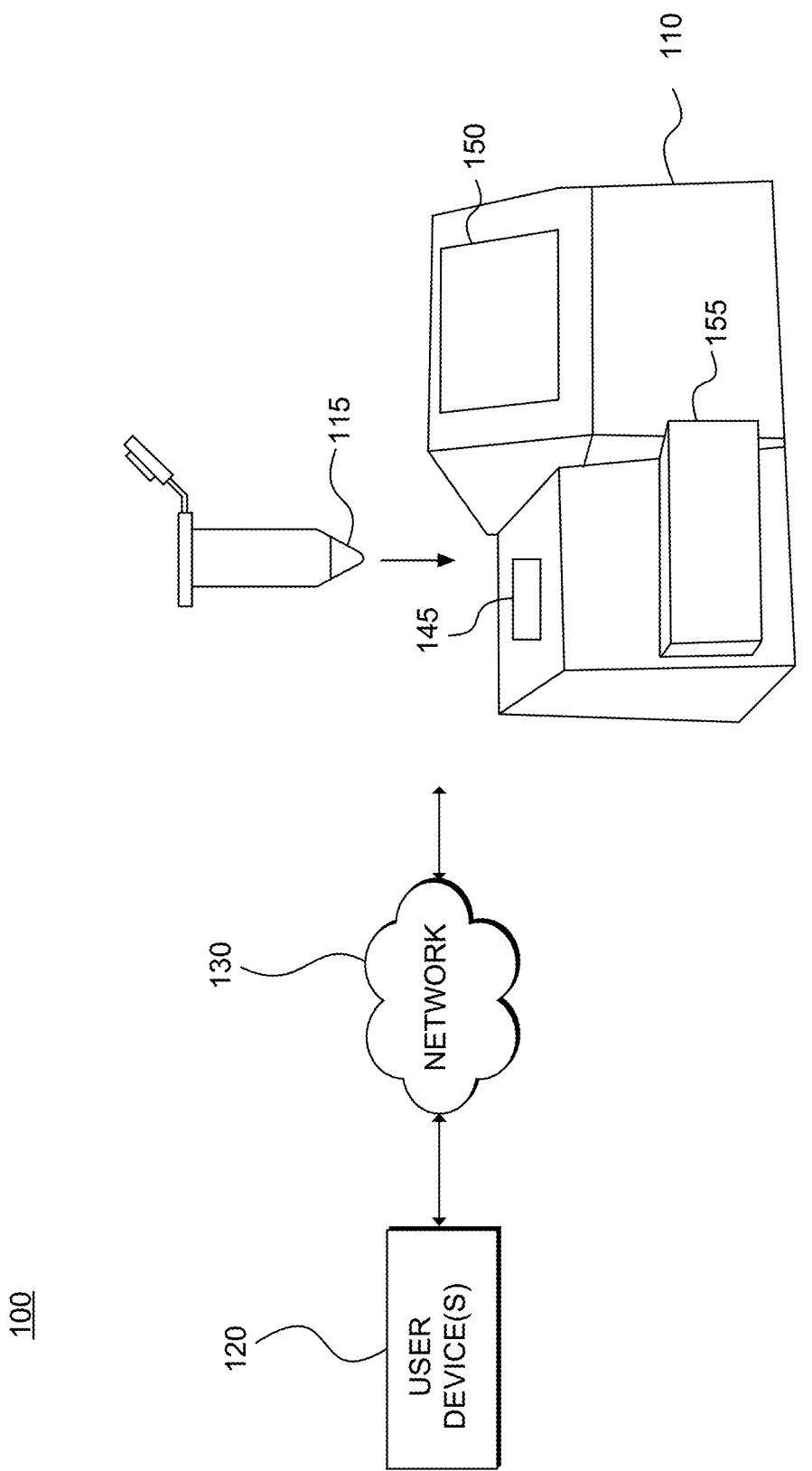
FIG. 1A illustrates an exemplary system for performing contamination analysis or training a CNN for contamination analysis, according to one or more embodiments of the present disclosure.

FIG. 1A depicts an exemplary environment/system in which a method of performing contamination analysis or training a CNN for contamination analysis can be implemented. The environment 100 can include a sequencing device 110 and one or more user devices 120 connected via a network 130.

The sequencing device 110 can include a sample container 115, a flow cell 145, a graphical user interface 150, and one or more loading trays 155. The sample container 115 can be configured to carry, hold, and/or store one or more test and/or training samples. The flow cell 145 can be placed in a flow cell holder of the sequencing device 110. The flow cell 145 can be a solid support that can be configured to retain and/or allow the orderly passage of reagent solutions over bound analytes. The graphical user interface 150 can enable user interactions with tasks (e.g., loading samples and buffers in the loading trays, or obtaining sequencing data that comprises a dataset with corresponding methylation pattern). For instance, once a user (e.g., a test subject, a training subject, a health professional) has provided the reagents and enriched fragment samples to the loading trays 155 of the sequencing device 110, the user can initiate sequencing by interacting with the graphical user interface 150 of the sequencing device 110. The sequencing device 110 can include one or more processing systems describe elsewhere herein.

User devices 120 can each be a computer system, such as a laptop or desktop computer, or a mobile computing device such as a smartphone or tablet. The user devices 120 can be communicatively coupled with the sequencing device 110 via network 125. Each user device can process data obtained from the sequencing device 110 for various applications such as generating a report regarding contamination analysis and/or a cancer condition to a user. The user can be a test subject, a training subject, or anyone can have access to the report (e.g., health professionals). The user devices 120 can include one or more processing systems describe elsewhere herein. The one or more user devices 120 can comprise a processing system and memory storing computer instructions that, when executed by the processing system, cause the processing system to perform one or more steps of any of the methods or processes disclosed herein.

The network 130 can be configured to provide communication between various components or devices shown in FIG. 1A. The network 130 can be implemented as the Internet, a wireless network, a wired network, a local area network (LAN), a Wide Area Network (WANs), Bluetooth, Near Field Communication (NFC), or any other type of network that provides communications between one or more components. The network 130 can be implemented using cell and/or pager networks, satellite, licensed radio, or a combination of licensed and unlicensed radio. The network 130 can be wireless, wired, or a combination thereof. The network 130 can be a public network (e.g., the internet), a private network (e.g., a network within an organization), or a combination of public and private networks.

Figure 1B:
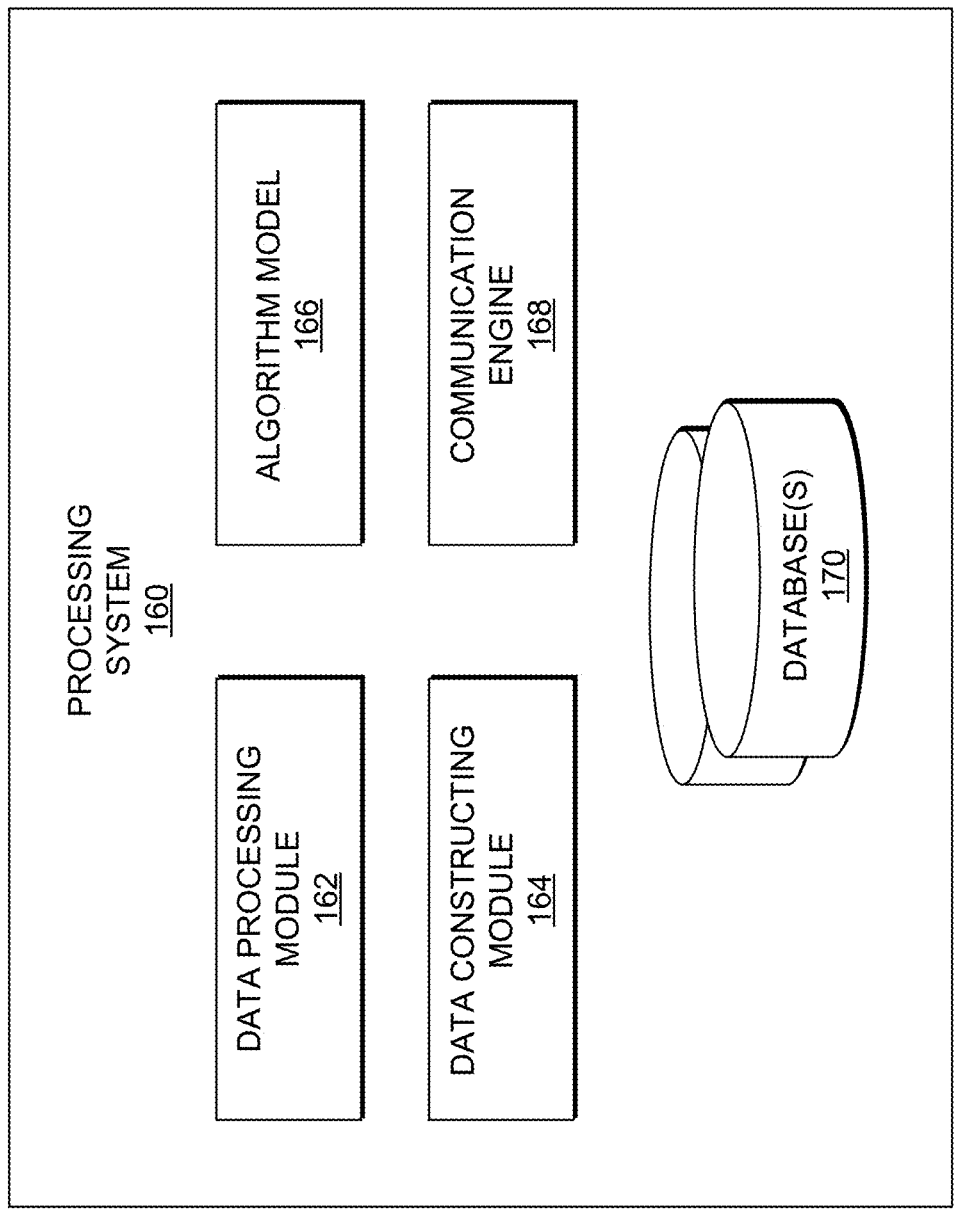
FIG. 1B illustrates an exemplary processing system for performing contamination analysis or training a CNN for contamination analysis, according to one or more embodiments of the present disclosure.

FIG. 1B depicts an exemplary block diagram of a processing system 160 for performing contamination analysis or training a CNN for contamination analysis. The processing system 160 can comprise one or more processors or servers that perform one or more steps of any of the methods or processes disclosed herein. The processing system 160 can include a plurality of models, engines, and modules. As shown in FIG. 1B, the processing system 160 can include a data processing module 162, a data constructing module 164, an algorithm model 166, a communication engine 168, and one or more databases 170.

The data processing module 162 can be configured to clean, process, manage, convert, and/or transform data obtained from the sequencing device 110. In one example, the data processing module can convert the data obtained from the sequencing device to data that can be used and/or recognized by other modules, engines, or models. For instance, the data constructing module 164 can construct output data from the data processing module 162. The data constructing module 164 can be configured to construct and/or further process data (e.g., process one or more images) obtained from the sequencing device 110 or any module, model, and engine of the processing system.

The algorithm model 166 can be configured to analyze, translate, convert, model, and/or transform data via one or more algorithms or models. Such algorithms or models can include any computational, mathematical, statistical, or machine learning algorithms, such as a classifier or a computational model described elsewhere herein. The classifier or the computational model can include at least one convolutional neural network. The classifier or computational model can comprise a pretrained model. The classifier or the computational model can include a layer that receives input values and is associated with at least one filter comprising a set of filter weights. This layer can compute intermediate values as a function of: (i) the set of filter weights and (ii) the plurality of input values. The classifier or the computational model can be stored in the one or more databases (e.g., non-persistent memory or persistent memory).

The communication engine 168 can be configured to provide interfaces to one or more user devices (e.g., user devices 120), such as one or more keyboards, mouse devices, and the like, that enable the processing system 160 to receive data and/or any information from the one or more user devices 120 or sequencing device 110.

The one or more databases 170 can include one or more memory devices configured to store data (e.g., a pre-trained model, training datasets, etc.). Additionally, the one or more databases 170 can be implemented as a computer system with a storage device. The one or more databases 170 can be used by components of a system or a device (e.g., a sequencing device 110) to perform one or more operations. The one or more databases 170 can be co-located with the processing system 160, and/or co-located with one another on the network. Each of the one or more of databases 170 can be the same as or different from other databases. Each of the one or more of databases 170 can be located in the same location as or be remote from other databases. The one or more databases may store additional modules and data structures not described above or elsewhere herein.

While a system in accordance with the present disclosure has been disclosed with reference to FIG. 1, methods in accordance with the present disclosure are now detailed with reference to FIGS. 2 and 13. Any of the disclosed methods can make use of any of the assays or algorithms disclosed in U.S. patent application Ser. No. 15/793,830, filed Oct. 25, 2017, and/or International Patent Publication No. PCT/US17/58099, having an International Filing Date of Oct. 24, 2017, each of which is hereby incorporated by reference, in order to determine a cancer condition in a test subject or a likelihood that the subject has the cancer condition. For instance, any of the disclosed methods can work in conjunction with any of the disclosed methods or algorithms disclosed in U.S. patent application Ser. No. 15/793,830, filed Oct. 25, 2017, and/or International Patent Publication No. PCT/US17/58099, having an International Filing Date of Oct. 24, 2017.

Training a Convolutional Neural Net for Contamination Analysis.

Figure 2:
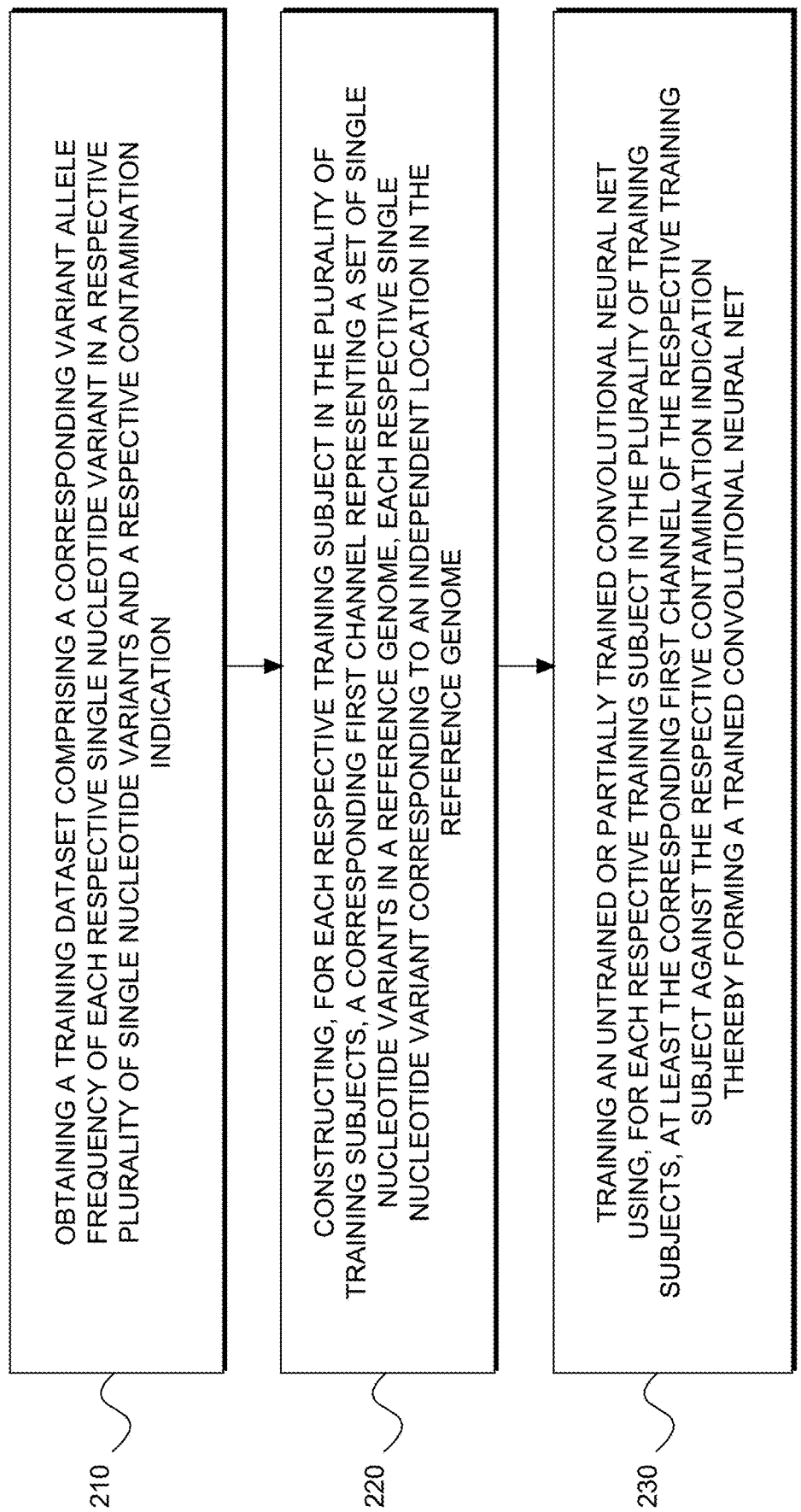
FIG. 2 illustrates an example flowchart of a method of performing contamination analysis or training a convolutional neural network (CNN) for contamination analysis, in accordance with some embodiments of the present disclosure.

FIG. 2 illustrates an overview of the techniques in accordance with some embodiments of the present disclosure. In the described embodiments, various methods of training a convolutional neural net for detecting contamination in samples (e.g., in images such as FIG. 3B) are described.

Referring to block 210 of FIG. 2, the method provides for training a convolutional neural net for contamination analysis (e.g., for analysis of the quality of biological samples). In some embodiments, this method is performed prior to downstream analysis (e.g., cancer diagnosis as described in Example 2) of a test biological sample for medical diagnosis or research purposes. The method can proceed by obtaining, in electronic format, a training dataset. The training dataset can comprise, for each respective training subject in a plurality of training subjects, a corresponding variant allele frequency of each respective single nucleotide variant in a respective plurality of single nucleotide variants. Each corresponding variant allele frequency can be determined by sequencing one or more nucleic acids in a respective biological sample obtained from the respective training subject. The training dataset can further comprise, for each respective training subject in the plurality of training subjects, and a respective contamination indication (e.g., an indication of a level of contamination of the respective biological sample). At least a first subset of the plurality of training subjects can have a first contamination indication value and a second subset of the plurality of training subjects can have a second contamination indication value. The first contamination indication value can be other than the second contamination indication value (e.g., there are at least two distinct contamination indication values for at least two distinct subsets in the plurality of training subjects).

In some embodiments, the first contamination indication value is selected from the set comprising 0, 0.1%, 0.3%, 0.5%, 1%, 5%, 10%, 15%, 20%, and 25%. In some embodiments, the second contamination indication value is selected from the set comprising 0, 0.1%, 0.3%, 0.5%, 1%, 5%, 10%, 15%, 20%, and 25%. In some embodiments, the first indication value is a first range of values and the second indication value is a second range of values. For instance, in some embodiments, the first indication value is between zero and ten percent and the second indication value is between ten percent and twenty percent.

In some embodiments, the training dataset comprises data for at least 20 training subjects, at least 40 training subjects, at least 60 training subjects, at least 80 training subjects, at least 100 training subjects, at least 150 training subjects, at least 200 training subjects, at least 250 training subjects, at least 300 training subjects, at least 350 training subjects, at least 400 training subjects, at least 450 training subjects, at least 500 training subjects, at least 600 training subjects, at least 700 training subjects, at least 800 training subjects, at least 900 training subjects, at least 1000 training subjects, at least 2000 training subjects, at least 3000 training subjects, at least 4000 training subjects, at least 5000 training subjects, at least 6000 training subjects, at least 7000 training subjects, at least 8000 training subjects, at least 9000 training subjects, or at least 10,000 training subjects. In some embodiments, the training data comprises data for between two and 100,000 training subjects.

In some embodiments, each training subject in the plurality of training subjects has a known cancer condition or disease condition (e.g., the plurality of training subjects is specific to a particular cancer or disease condition or the plurality of training subjects includes multiple cancer or disease conditions). In some embodiments, one form of known cancer condition is absence of the cancer condition. In some embodiments, one form of known disease condition is absence of the disease condition.

In some embodiments, the respective contamination for a corresponding training subject is simulated (e.g., non-contaminated samples are artificially contaminated). In some embodiments, the contamination simulation comprises, for each training subject in the plurality of training subjects, selecting the respective contamination indication value (e.g., randomly selected from the set of contamination indication values), and for each respective single-nucleotide variants in the respective plurality of single nucleotide variants, obtaining, a respective plurality of sequence reads from the respective biological sample, and selecting a percentage of sequence reads from the training subject and a percentage of sequence reads from a reference set to determine the corresponding variant allele frequency. In some embodiments, the contamination indication is used to determine the percentage of sequence reads used from the reference set (e.g., the contamination percentage).

In some embodiments, the reference set comprises a composite of a set of reference samples (e.g., represent an average variant allele frequency for a reference set of subjects—e.g., from a publically available dataset of individuals). The combination of reference set sequence reads and training subject sequence reads can provide the respective contamination level of the training subject. In this way, the respective contamination indications for training can be known exactly for each training subject. This also allows the use of a set of non-contaminated training samples for training to detect contamination.

In some embodiments, the first biological sample is a liquid biological sample (e.g., of the test subject) and each respective nucleic acid fragment sequence in the first plurality of nucleic acid fragment sequences represents all or a portion of a respective cell-free nucleic acid molecule in a population of cell-free nucleic acid molecules in the liquid biological sample.

In some embodiments, the first biological sample is a tissue biological sample (e.g., of the test subject) and each respective nucleic acid fragment sequence in the first plurality of nucleic acid fragment sequences represents all or a portion of a respective nucleic acid molecule in a population of nucleic acid molecules in the tissue sample. In some embodiments, the tissue sample is a tumor sample from the test subject.

In some embodiments, the first biological sample comprises or consists of blood, whole blood, plasma, serum, urine, cerebrospinal fluid, fecal, saliva, sweat, tears, pleural fluid, pericardial fluid, or peritoneal fluid of the subject. In such embodiments, the first biological sample may include the blood, whole blood, plasma, serum, urine, cerebrospinal fluid, fecal, saliva, sweat, tears, pleural fluid, pericardial fluid, or peritoneal fluid of the subject as well as other components (e.g., solid tissues, etc.) of the subject.

In some embodiments, for example, if the biological sample for a respective training subject is derived from cell-free nucleic acids, it is advantageous that the cell-free nucleic acids exhibit an appreciable tumor fraction. In some embodiments, the corresponding tumor fraction, with respect to the respective training subject is at least two percent, at least five percent, at least ten percent, at least fifteen percent, at least twenty percent, at least twenty-five percent, at least fifty percent, at least seventy-five percent, at least ninety percent, at least ninety-five percent, or at least ninety-eight percent.

In some embodiments, such biological samples comprise or contain cell-free nucleic acid fragments (e.g., cfDNA fragments). In some embodiments, the biological sample is processed to extract the cell-free nucleic acids in preparation for sequencing analysis. By way of a non-limiting example, in some embodiments, cell-free nucleic acid fragments are extracted from a biological sample (e.g., blood sample) collected from a subject in K2 EDTA tubes. In the case where the biological samples are blood, the samples are processed within two hours of collection by double spinning of the biological sample first at ten minutes at 1000 g, and then the resulting plasma is spun ten minutes at 2000 g. The plasma can then be stored in 1 ml aliquots at −80° C. In this way, a suitable amount of plasma (e.g. 1-5 ml) can be prepared from the biological sample for the purposes of cell-free nucleic acid extraction. In some such embodiments, cell-free nucleic acids are extracted using the QIAamp Circulating Nucleic Acid kit (Qiagen) and eluted into DNA Suspension Buffer (Sigma). In some embodiments, the purified cell-free nucleic acid is stored at −20° C. until use. Other equivalent methods can be used to prepare cell-free nucleic acid from biological methods for the purpose of sequencing, and all such methods are within the scope of the present disclosure.

In some embodiments, the cell-free nucleic acid fragments that are obtained from a biological sample are any form of nucleic acid defined in the present disclosure, or a combination thereof. For example, in some embodiments, the cell-free nucleic acid that is obtained from a biological sample is a mixture of RNA and DNA.

Sequencing of cell-free nucleic acid fragments. After obtaining a plurality of cell-free nucleic acid fragments from a biological sample, the cell-free nucleic acid fragments can be sequenced. In some embodiments, the sequencing comprises whole-genome sequencing. In some embodiments, the sequencing comprises targeted sequencing using a plurality of nucleic acid probes. In some embodiments, the sequencing is performed as described below in Example 1. In some embodiments, the sequencing comprises methylation sequencing. In some embodiments, the methylation sequencing is whole-genome methylation sequencing. In some embodiments, the methylation sequencing is targeted DNA methylation sequencing using a plurality of nucleic acid probes. In some embodiments, the plurality of nucleic acid probes comprises one hundred or more probes. In some embodiments, the plurality of nucleic acid probes comprises 100 or more, 200 or more, 300 or more, 400 or more, 500 or more, 600 or more, 700 or more, 800 or more, 900 or more, 1000 or more, 2000 or more, 3000 or more, 4000 or more 5000 or more, 6000 or more, 7000 or more, 8000 or more, 9000 or more, 10,000 or more, 25,000 or more, or 50,000 or more probes.

In some embodiments, the methylation sequencing detects one or more 5-methylcytosine (5 mC) and/or 5-hydroxymethylcytosine (5 hmC) in respective nucleic acid fragments in the first plurality of nucleic acid fragments. In some embodiments, the methylation sequencing comprises the conversion of one or more unmethylated cytosines or one or more methylated cytosines, in the nucleic acid fragments in the first plurality of nucleic acid fragments, to a corresponding one or more uracils. In some embodiments, the one or more uracils are converted during amplification and detected during the methylation sequencing as one or more corresponding thymines. In some embodiments, the conversion of one or more unmethylated cytosines or one or more methylated cytosines comprises a chemical conversion, an enzymatic conversion, or combinations thereof.

In some such embodiments, prior to sequencing, the cell-free nucleic acid fragments are treated to convert unmethylated cytosines to uracils. In some embodiments, the method uses a bisulfite treatment of the DNA that converts the unmethylated cytosines to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA)) is used for the bisulfite conversion. In some embodiments, the conversion of unmethylated cytosines to uracils is accomplished using an enzymatic reaction. For example, the conversion can use a commercially available kit for the conversion of unmethylated cytosines to uracils, such as APOBEC-Seq (NEBiolabs, Ipswich, MA).

From the converted cell-free nucleic acid fragments, a sequencing library can be prepared. Optionally, the sequencing library can be enriched for cell-free nucleic acid fragments, or genomic regions, that are informative for cell origin using a plurality of hybridization probes. The hybridization probes can be short oligonucleotides that hybridize to particularly specified cell-free nucleic acid fragments, or targeted regions, and enrich for those fragments or regions for subsequent sequencing and analysis. In some embodiments, hybridization probes are used to perform targeted, high-depth analysis of a set of specified CpG sites that are informative for cell origin. Once prepared, the sequencing library or a portion thereof can be sequenced to obtain a plurality of sequence reads.

In this way, in some embodiments, more than 1000, 5000, 10,000, 15,000, 100,000 or one million sequence reads are recovered from the biological sample. In some embodiments, the sequence reads recovered from the biological sample provide a coverage rate of 1× or greater, 2× or greater, 5× or greater, 10× or greater, or 50× or greater for at least two percent, at least five percent, at least ten percent, at least twenty percent, at least thirty percent, at least forty percent, at least fifty percent, at least sixty percent, at least seventy percent, at least eighty percent, at least ninety percent, at least ninety-eight percent, or at least ninety-nine percent of the genome of the subject. In embodiments where the biological sample comprises or contains cell-free nucleic acid fragments, the resulting sequence reads are thus of cell-free nucleic acid fragments.

In some embodiments, any form of sequencing can be used to obtain the sequence reads from the cell-free nucleic acid fragments obtained from the biological sample. These sequencing methods can comprise, but are not limited to, high-throughput sequencing systems such as the Roche 454 platform, the Applied Biosystems SOLID platform, the Helicos True Single Molecule DNA sequencing technology, the sequencing-by-hybridization platform from Affymetrix Inc., the single-molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used to obtain sequence reads from the cell-free nucleic acid obtained from the biological sample.

In some embodiments, sequencing-by-synthesis and reversible terminator-based sequencing (e.g., Illumina's Genome Analyzer; Genome Analyzer II; HISEQ 2000; HISEQ 2500 (Illumina, San Diego Calif.)) is used to obtain sequence reads from the cell-free nucleic acid obtained from the biological sample. In some such embodiments, millions of cell-free nucleic acid (e.g., DNA) fragments are sequenced in parallel. In one example of this type of sequencing technology, a flow cell is used that contains an optically transparent slide with eight individual lanes on the surfaces of which are bound oligonucleotide anchors (e.g., adaptor primers). A flow cell can often be a solid support that is configured to retain and/or allow the orderly passage of reagent solutions over bound analytes. In some instances, flow cells are planar in shape, optically transparent, generally in the millimeter or sub-millimeter scale, and often have channels or lanes in which the analyte/reagent interaction occurs. In some embodiments, a cell-free nucleic acid sample can include a signal or tag that facilitates detection. In some such embodiments, the acquisition of sequence reads from the cell-free nucleic acid obtained from the biological sample includes obtaining quantification information of the signal or tag via a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

In some embodiments, the sequence reads are corrected for background copy number. For instance, sequence reads that arise from chromosomes or portions of chromosomes that are duplicated in the subject are corrected for this duplication. This can be done by normalizing before running this inference.

Variant allele frequencies. In some embodiments, a variant allele frequency is determined for each respective single nucleotide variant (e.g., an allele position) in the plurality of single nucleotides for a respective training subject by using the first plurality of nucleic acid fragment sequences in the respective biological sample for the training subject (e.g., by calculating a ratio of nucleic acid fragment sequences). In some embodiments, each corresponding variant allele frequency is between 0 and 1 (e.g., each single nucleotide variant is supported by a ratio of between 0 and 1 of the total nucleic acid fragment sequences that are mapped to the respective single nucleotide variant). For instance, consider the case where there are 40 fragments in a respective subject that map to a particular allele position that is characterized by reference allele and an alternate allele and, of these 40 fragments, 30 fragments have the reference allele and 10 fragments have the alternate allele. In this case, the variant allele frequency for this particular allele position is 10/40 or 0.25.

Referring to block 206, in some embodiments, the training dataset comprises a plurality of subsets of training subjects (e.g., subsets of the plurality of training subjects), where each subset of training subjects has a respective contamination indication value. In some embodiments, the plurality of subsets of the plurality of training subjects comprises at least 2 subsets, at least 3 subsets, at least 4 subsets, at least 5 subsets, at least 6 subsets, at least 7 subset, at least 8 subsets, at least 9 subsets, or at least 10 subsets of training subjects. In some embodiments, each subset has a respective contamination indication value that distinct from other contamination indications for other subsets. In some embodiments, the respective contamination indication value for each subset of training subjects is between 0% and 50%.

In some embodiments, each training subject in the plurality of training subjects is part of the CCGA study. See Example 3 for further details on the CCGA study.

In some embodiments, each subset of training subjects comprises at least 20 training subjects, at least 40 training subjects, at least 60 training subjects, at least 80 training subjects, at least 100 training subjects, at least 150 training subjects, at least 200 training subjects, at least 250 training subjects, at least 300 training subjects, at least 400 training subjects, at least 500 training subjects, at least 600 training subjects, at least 700 training subjects, at least 800 training subjects, at least 900 training subjects, or at least 1000 training subjects.

In some embodiments, each training subject in the plurality of training subjects is human. In some embodiments, the reference genome comprises a human genome.

In some embodiments, for a respective training subject, the corresponding plurality of single nucleotide variants comprises each single nucleotide variant measured in the respective biological sample of the respective training subject. In some embodiments, the corresponding set of single nucleotide variants comprises each possible single nucleotide variant of the reference genome.

In some embodiments, the method proceeds by constructing, for each respective training subject in the plurality of training subjects, a corresponding first channel 142-1 (e.g., represented as an image) representing a corresponding set of single nucleotide variants in a reference genome, where each respective single nucleotide variant corresponds to an independent location in the reference genome. The respective first channel can comprise a first plurality of parameters. In some embodiments, the plurality of parameters comprises two or more, three or more, 10 or more, between 2 and 10000, or less than 10000 parameters). Each respective parameter in the first plurality of parameters represents a single nucleotide variant allele frequency of a corresponding single nucleotide variant in the set of single nucleotide variants for the respective training subject. For instance, in some embodiments, the respective parameter for a single nucleotide variant allele frequency of the respective single nucleotide variant is, in fact, the observed single nucleotide variant allele frequency of the respective single nucleotide variant for the respective training subject.

Figure 3A:
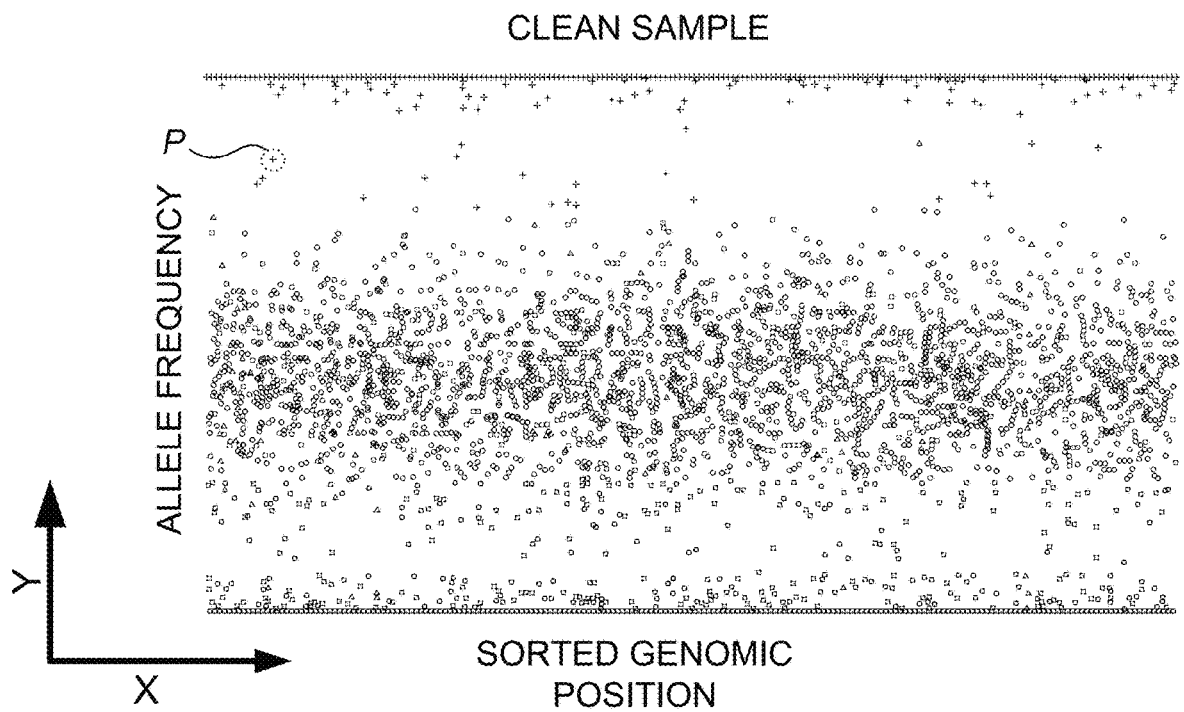
FIGS. 3A and 3B illustrate example clean and contaminated sample images, in accordance with some embodiments of the present disclosure.
Figure 3B:
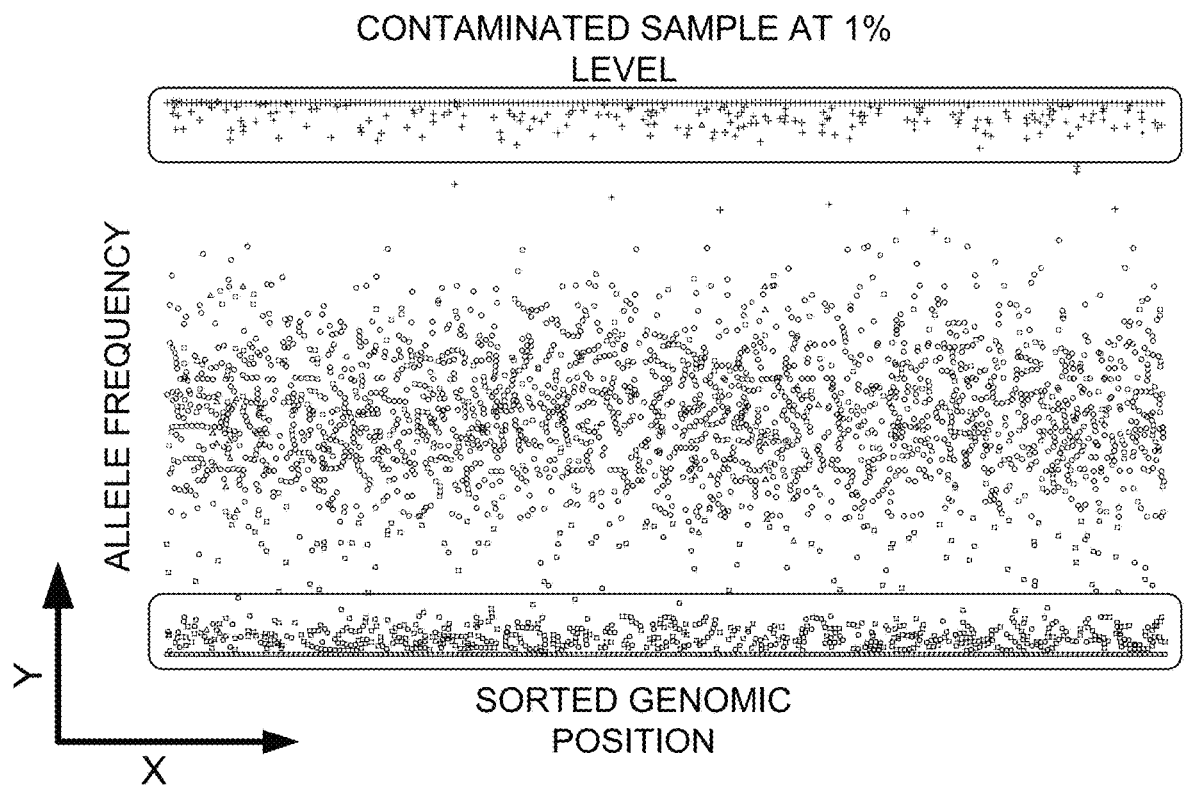

In some embodiments, the first plurality of parameters for the corresponding set of single-nucleotide variants in the first channel are ordered in accordance with a respective position of each single nucleotide variant in the corresponding set of single-nucleotide variants in the reference genome (see, e.g., the x-axis of FIGS. 3A, and 3B). For instance, FIG. 3A represents a channel in which the x-axis is the genomic position of each respective single nucleic acid variant in a reference genome and the y-axis is the allele frequency of the respective nucleic acid variant. This can be illustrated by parameter P in FIG. 3A which is plotted within the channel in accordance with an x-coordinate value (determined by the position of the single nucleotide variant that parameter P represents in the reference genome) and a y-coordinate value (determined by the observed allele frequency of the single nucleotide variant that parameter P represents in the reference subject that FIG. 3A represents, on a scale between zero and one hundred percent). Thus, in some embodiments, the channel illustrated in two dimensions in FIG. 3A may be inputted as first-channel 142-1 into the convolutional neural network of FIG. 10.

In some embodiments, a single channel, represented as the two-dimensional images illustrated in FIGS. 3A and 3B is used. However, the present disclosure is not so limited. In some embodiments, more than one channel may be used. For instance, in some embodiments, in addition to the first channel, a second channel may be used. In some embodiments, the second channel may be in the form of an additional image, where the first dimension once again represents the genomic position (of each of the corresponding single nucleotide variants), and the second dimension now represents another characteristic such as (i) the number of fragments observed in the training subject from which the variant allele frequency (of each corresponding single nucleotide variant) is drawn, (ii) an error statistic of each respective single nucleotide variant, or (iii) a parameter indicating a loss of heterozygosity status for each respective single nucleotide variant.

Embodiment that uses three separate channels may be applicable to transfer learning implementations where the convolutional neural network was previously trained on pixelated color images where each pixel within the image includes a separate red, green, and blue value. In such embodiments, the "red" pixel value of each pixel may be assigned to indicate the allele frequency of the respective nucleic acid variant, the "green" pixel of each pixel may be assigned to indicate the number of fragments observed in the training subject from which the variant allele frequency (of the corresponding single nucleotide variant) may be drawn. These embodiments can further be extended to the final RGB pixel value, "blue", which can be assigned to indicate another aspect of each particular SNV of a particular training subject, such as an error statistic in sequencing or an indication of loss of heterozygosity status.

Figure 12:
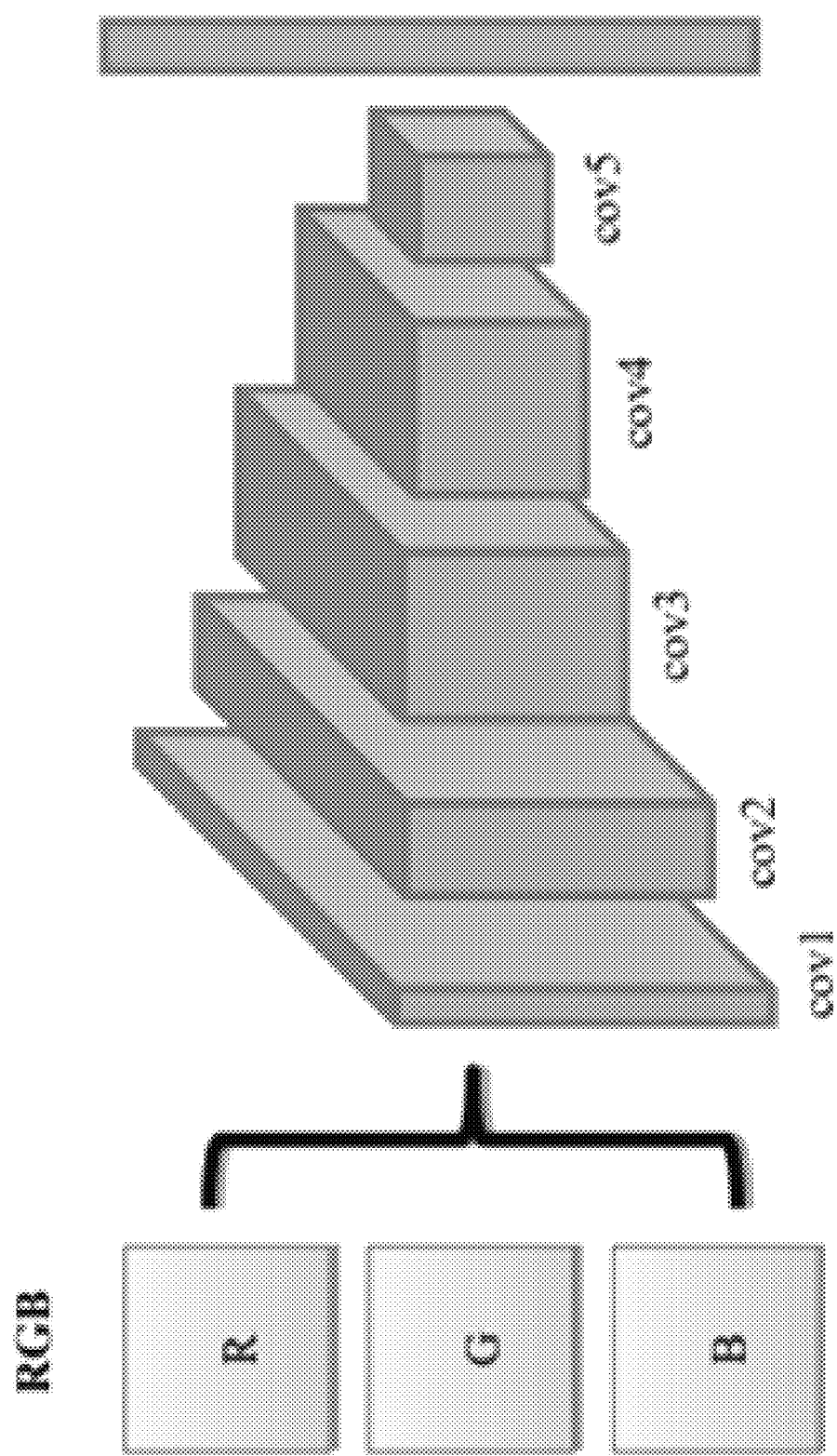
FIG. 12 illustrates a convolutional neural network for handling data encoded into three separated channels.

FIGS. 3A and 3B illustrate one way of representing the variant allele frequency for each SNV. In FIGS. 3A and 3B, the cross shape represents red color, the square shape represents blue color, and the circle shape represents the green color. In some transfer learning embodiments in which the pre-trained classifier may be trained on RGB images and three channels may be used, the observed values for the first channel (e.g., the allele frequency for each respective SNV, ranging from 0 to 100) may be scaled to between, for example, about 380 nm and about 500 nm which is the wavelength range of blue, the observed values for the second channel (e.g., the number of fragments observed in the training subject from which each respective variant allele frequency is drawn) may be scaled to between, for example, about 500 nm and about 590 nm which is the wavelength range of green, and the observed values for the third channel (e.g., an error statistic of each respective SNV) may be scaled to between, for example, about 590 nm and about 740 nm which is the wavelength range of red. In some embodiments, the three different channel values for each SNV may be arranged together to form a pixel, and this data representing the SNVs may be further arranged in a two-dimensional image that is presented to the pre-trained classifier. FIG. 12 illustrates an example situation in which a single such pixel, representing a particular SNV in the set of SNVs, may be presented to a convolutional neural network. In FIG. 12, R represents red, G represents green, and B represents blue. Additionally, in FIG. 12, cov1 represents the first convolutional layer, cov2 represents the second convolutional layer, cov3 represents the third convolutional layer, cov4 represents the fourth convolutional layer, and cov5 represents the fifth convolutional layer. While FIG. 12 illustrates the presentation of just one such pixel to the convolutional neural network, in practice a plurality of pixels, arranged in the form of a two dimensional image, where each pixel value contains three values for three channels may be presented to the convolutional neural network. In some embodiments, there may be a plurality of such two-dimensional images, where each such image may represent the above-described SNV values (e.g., variant allele frequency). Such an embodiment may be useful in situations where the convolutional neural network has already been trained on unrelated RGB pixelated images, such as the ResNet34 convolutional neural network.

Figure 5:
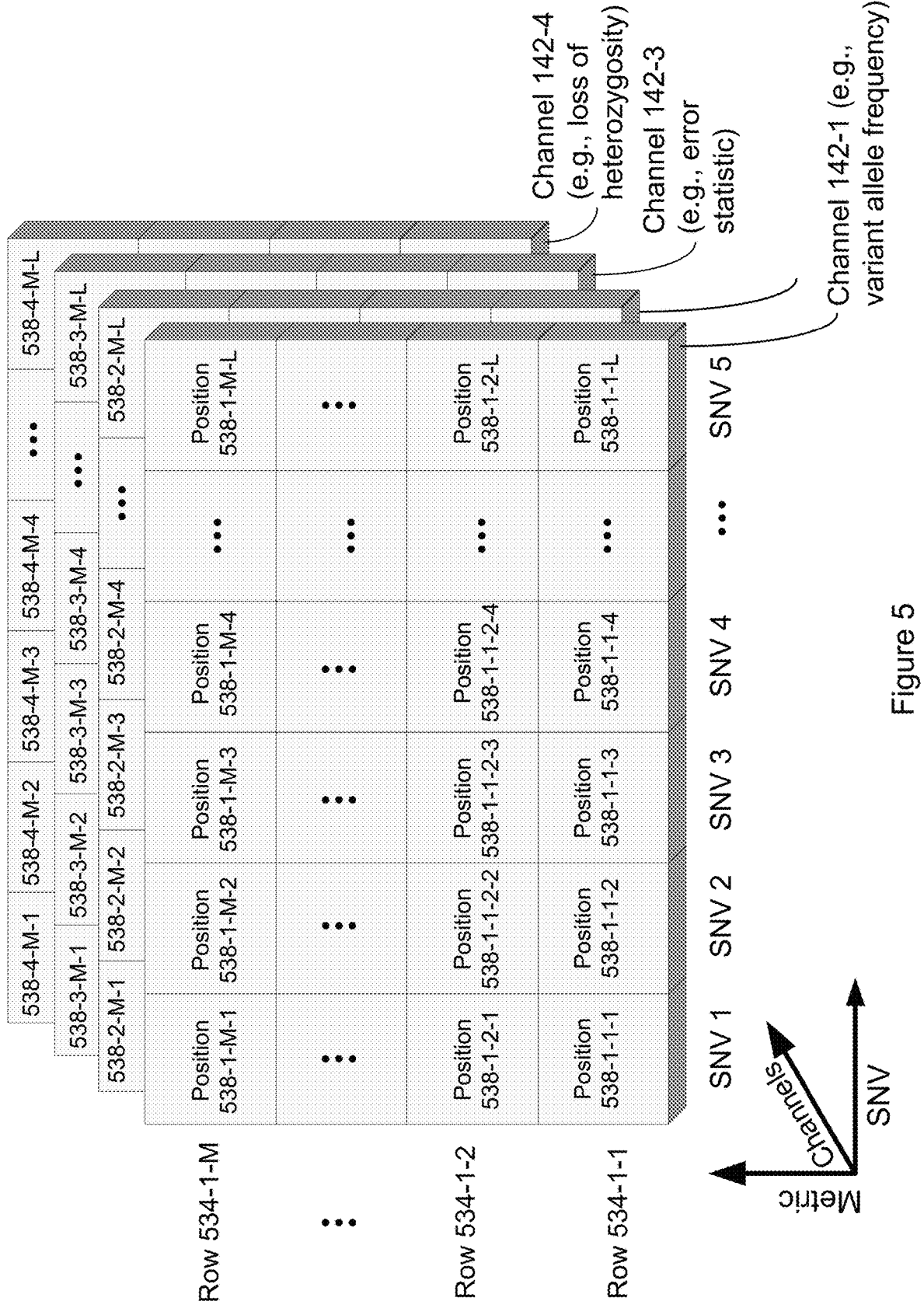
FIG. 5 illustrates a plurality of channels in accordance with some embodiments of the present disclosure.

FIG. 5 illustrates another way in which a plurality of channels 142 corresponding to each SNV in the set of SNVs can be inputted into a convolutional neural network. As depicted in FIG. 5, the first channel 142-1 ("red") comprises the plurality of rows 534-1-1, 534-1-2 to 534-1-M, where M is a positive integer. Considering SNV 1, the variant allele frequency for SNV 1 in a respective training subject can be represented by assigning the position, in the column represented by 538-1-1-1 through 538-1-M-1 that corresponds to this variant allele frequency, a first value demarking the variant allele frequency of SNV 1 while all other positions in column 538-1-1-1 through 538-1-M-1 may have a second value demarking that the variant allele frequencies represented by these other positions do not correspond to the variant allele frequency of SNV 1 in a respective training subject. For instance, if the variant allele frequency is 0.58, the position in the column 538-1-1-1 through 538-1-M-1 that represents 0.58 may be given a first value and all other positions in the column may be given a second value. In other words, the first channel 142-1 may be encoded as illustrated in FIGS. 3A, and 3B. Likewise, the two-dimensional positions in each channel 142-2 ("Green"), and 142-3 ("Blue") may be populated for each respective SNV with other characteristics of the SNVs, such as sequencing depth, sequencing error statistics, or loss of heterozygosity. In some embodiments, the encoding of the second and higher channels may be performed by placing the value for a particular SNV in the position in the second channel that corresponds to the position that was set to the first value for this SNV in the first channel. For example, in the situation, if the variant allele frequency is 0.58, the position in the column 538-1-1-1 through 538-1-M-1 that represents 0.58 may be given a first value and all other positions in the column may be given a second value. The position in the second channel that corresponds to the position 0.58 could then be populated with a scalar value that represents the sequencing depth for this SNV in the respective training subject. So, for example, if the position 538-1-45-1 is assigned a first value to represent the variant allele frequency of SNV 1 for the respective subject while all other positions were assigned a second value in the first channel 141-1, the position 538-2-45-1 may be assigned the sequencing depth of SNV 1 for the respective subject in channel 142-2 while the position 538-3-45-1 may be assigned the SNV error statistic for SNV 1 for the respective subject in channel 143-3 and so forth. In such embodiments, the values in the first channel are binary and the values in the subsequent channels may range in a scalar manner.

As illustrated in FIG. 5, the present disclosure is not limited to three channels representing the three colors of an RGB signal that may be used in some pretrained classifiers. In some embodiments, additional channels may be used. For instance, in FIG. 5, four two-dimensional channels may be used. As illustrated in FIG. 5, one axis of each of these channels may represent the ordered set of SNVs, while the other axis represents a metric such as variant allele frequency. The second channel may represent the number of fragments observed in the training subject from which the variant allele frequency (of the corresponding single nucleotide variant) is drawn (e.g., single nucleotide variant depth of each respective single nucleotide variant in the set of single nucleotide variants), the third channel may represent an error statistic of each respective single nucleotide variant in the set of single nucleotide variants for the respective subject, and the fourth channel may represent a loss of heterozygosity status for each respective single nucleotide variant in the set of single nucleotide variants.

Referring to FIGS. 3A and 3B, in some embodiments, the dimension representing variant alleles is fixed across the training population meaning that, if a particular training subject does not have enough data for a particular single nucleotide variant represented on the axis, that position on the axis (column or row associated with the single nucleotide variant for a given channel) is simply left blank within the channel. In some embodiments, the dimension representing variant alleles is not fixed across the training population.

In some embodiments, as illustrated in FIGS. 3A and 3B, in some embodiments a channel represents a two-dimensional pixelated image where individual pixels represent a unique combination of variant allele frequency and single nucleotide variant identity. For instance, referring once again to element P of FIG. 3A, this is a pixel in the plurality of pixels that represents a particular combination of a variant allele frequency and a particular single nucleotide variant identity. For any given single nucleotide variant identity, there can be any number of variant allele frequencies. For example, consider the case where variant allele frequency is between zero and one. The values from zero to one can be represented by any number of increments, such as, for example, increments of 0.01. In this case, for a particular single nucleotide variant, there would be 100 different possible increments for the variant allele frequency and the observed variant allele frequency would be matched to the increment that best matches. For instance, if the observed variant allele frequency for a particular single nucleotide variant is 0.534, and the channel has variant allele frequency increments of 0.01 between 0 and 1, the observed variant allele frequency can be matched to the increment of 0.53 since this best matches the observed 0.534. Thus, although there are 100 possible pixels for the particular single nucleotide variant in the channel (e.g., in the form of a row or column of pixels), the pixel at 0.53 can be populated. In some embodiments, those pixels in a channel that actually represent an observed single nucleotide variant/variant allele frequency for the corresponding subject are set to one value and those pixels that do not represent an observed single nucleotide variant/variant allele frequency for the corresponding subject are set to another value. In some embodiments, the first value is a logical "one" and the second value is a logical "zero." In some embodiments, the first value is a logical "zero" and the second value is a logical "one." In some embodiments, variant allele frequencies are represented by ten incremental values, one hundred incremental values, one thousand incremental values, or 10,000 incremental values. In some embodiments, a channel represents one hundred or more nucleotide variants, one thousand or more one hundred or more nucleotide variants, or ten thousand or more nucleic variants. In a non-limiting example where a channel represents 1000 nucleotide variants and there are 1000 different incremental allele frequency values for each nucleotide variant, the channel comprises 1000×1000 pixels, or 1,000,000 pixels, each pixel for a different combination of variant/allele frequency. Accordingly, in some embodiments, a channel comprises 100 to 1000 pixel values, 1000 to 1,000,000 pixel values, $1\times10^6$ to $1\times10^7$ pixel values, or $1\times10^7$ to $1\times10^8$ or more pixel values.

Figure 4A:
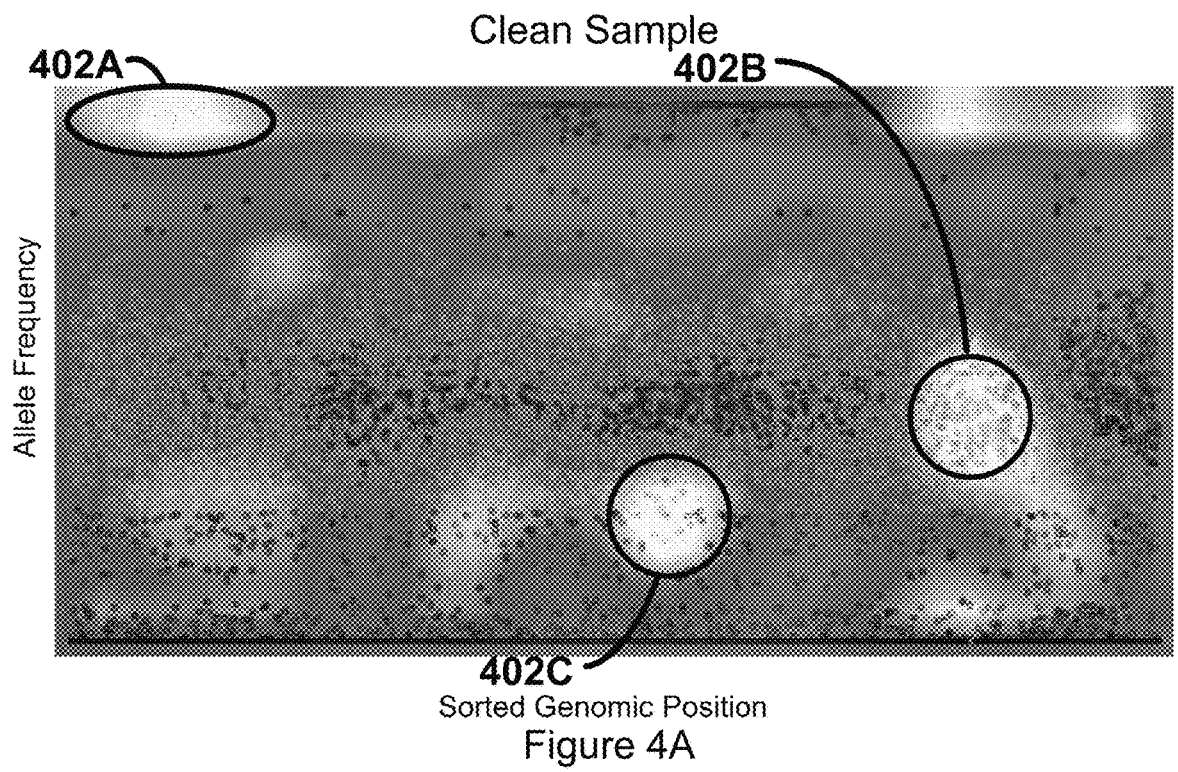
FIGS. 4A and 4B illustrate example of activation heatmaps drawn from a convolutional neural network for clean and contaminated sample images respectively, with informative regions highlighted, in accordance with some embodiments of the present disclosure.
Figure 4B:
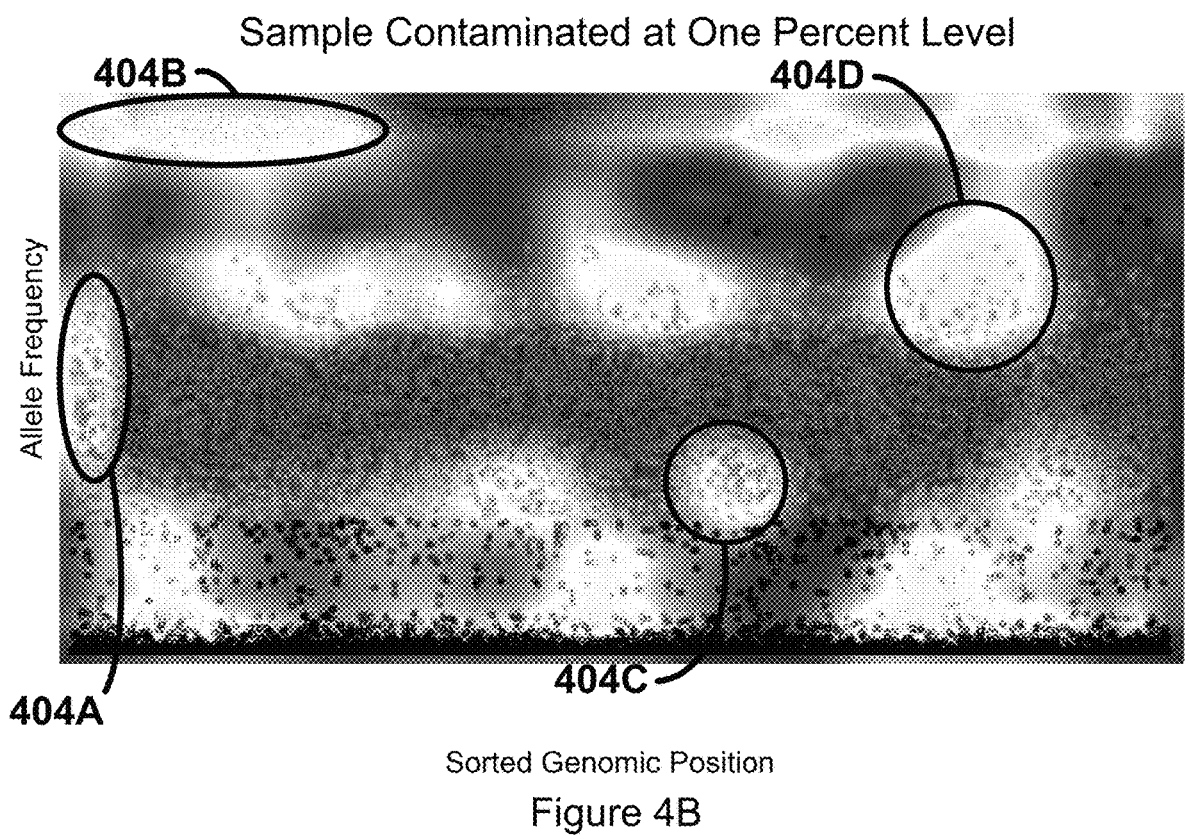

The ordering of the single nucleic variant/variant allele frequency into an N-dimensional channel, where N is a positive integer such as two, takes advantage of the ability for a convolutional neural network to learn localized patterns (e.g., samples from different subjects can be comparable to each other) using spatial input. For instance, as discussed above, SNVs can be arranged in the first channel, so that SNVs that appear in nearby pixels can also be present in neighboring locations in the reference genome. This can be seen in FIGS. 4A and 4B. FIG. 4A represent an activation heatmap drawn from a convolutional neural network of the present disclosure upon presentation with a clean sample. The high-intensity locations 402 in FIG. 4A are hallmarks of a non-contaminated sample. FIG. 4B represents an activation heatmap drawn from the same convolutional neural network as FIG. 4A upon presentation with a one percent contaminated sample. The high-intensity locations 404 in FIG. 4B are hallmarks of a contaminated sample. As can be seen from the comparison of FIGS. 4A and 4B, the ordering of SNVs that are adjacent to each other in the reference genome may be advantageous because it may allow for the retention of genomic information (e.g., that nearby SNVs from a contaminating sample can be observed together due to linkage disequilibrium).

Referring to block 214, in some embodiments, each single nucleic variant in the corresponding set of single-nucleotide variants in the first channel is fixed to a respective position along an axis of the first channel that represent variant identity (e.g., there is a predefined location along the axis representing variant identity for each single nucleotide variant, regardless of which single nucleotide variants are present in the corresponding plurality of single nucleotide variants for a respective training subject). By fixing each SNV to a specific location along this axis, the trained convolutional neural net is able, in some embodiments, to learn which SNVs are consistently "noisy" and ignore those variants when making predictions. This particular ordering may be advantageous because fixing SNVs to locations along an axis representing variant identity can improve training efficiency (e.g., the training may use less time and/or less computing power) by having a predefined location along an axis for each and every SNV in the set of SNVs.

In some embodiments, the method further comprises constructing, for each respective training subject in the plurality of training subjects, a corresponding second channel comprising a second plurality of parameters. The second plurality of parameters may include a respective parameter for a single nucleotide variant depth of each respective single nucleotide variant in the set of single nucleotide variants. Thus, in such embodiments, for a given training subject for a given single nucleotide variant, a first parameter in the first plurality of parameters may encode a single nucleotide variant allele frequency of a single nucleotide variant corresponding to the first parameter while a corresponding second parameter in the second plurality of parameters may encode a sequencing depth for this single nucleotide variant. In some embodiments, each parameter in the second plurality of parameters may uniquely correspond to a parameter in the first plurality of parameters, and each parameter in the first plurality of parameters may uniquely correspond to a single nucleotide variant in the set of single nucleotide variants.

In some embodiments, the respective parameter in the second plurality of parameters for a single nucleotide variant depth comprises a mapping depth (e.g., of nucleic acid fragment sequences that map to the SNV from the biological sample of the training subject) of at least 1, at least 2, at least 3, at least 4, at least 5, at least 6, at least 7, at least 8, at least 9, at least 10, at least 15, at least 20, at least 30, or at least 40. In some embodiments, the respective parameter in the second plurality of parameters for a single nucleotide variant depth comprises a mapping depth (e.g., of nucleic acid fragment sequences that map to the SNV from the biological sample of the training subject) of at most 100, 90, 80, 70, 60, 50, 40, 30, 20, 10, 9, 8, 7, 6, 5, 4, 3, 2, or 1.

In some embodiments, the second channel may be layered next to the first channel thus forming a composite channel. For instance, this composite channel may have the form of channels 142-1 and 142-2 illustrated in FIG. 5. In some embodiments, this composite channel may be inputted into the convolutional neural network. Thus, referring to FIG. 10, in some embodiments, there may be a single stack of layers in the convolutional neural network (e.g., for the three-dimensional composite channel) and no other channels or stack of layers. In other words, in such embodiments, first channel 142-1 may be a single three-dimensional composite channel and the stacks of layers in the convolutional neural network corresponding to channels 142-2 and 142-3 illustrated in FIG. 10 may not be present in the convolutional neural network. In other embodiments, the second channel may not be layered next to the first channel but rather may be independently inputted into the convolutional neural network. In such embodiments, the second channel may have a first dimension that represents the genomic position (of the corresponding single nucleotide variant) and a second dimension that represents the number of fragments observed in the training subject from which the variant allele frequency (of the corresponding single nucleotide variant) is drawn (e.g., single nucleotide variant depth of each respective single nucleotide variant in the set of single nucleotide variants). Thus, referring to FIG. 10, in some embodiments, there may be two stacks of layers (e.g., one for the first two-dimensional channel 142-1 and another for the second two-dimensional channel 142-2) and no other stacks of layers.

Figure 10:
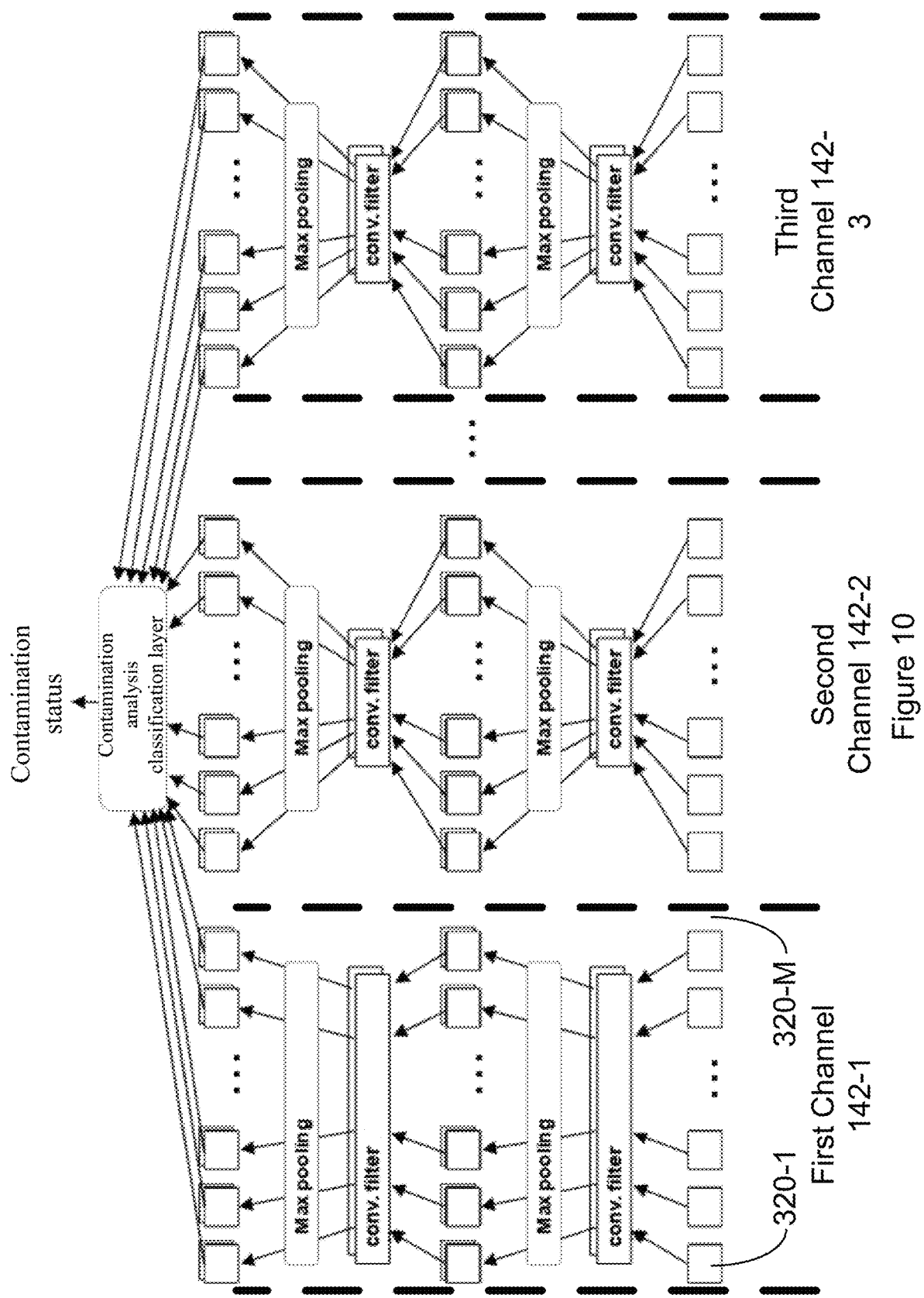
FIG. 10 illustrates a convolutional neural network in accordance with an embodiment of the present disclosure.

The arrangement of convolutional filters and pooling layers, and the number such filters and layers in the convolutional neural network illustrated in FIG. 10 are exemplary and other embodiments of the present disclosure may include other arrangements of such layers.

In some embodiments, training an untrained or partially trained convolutional neural net further comprises using, for each respective training subject in the plurality of training subjects, at least the corresponding second channel of the respective training subject, as input to the untrained or partially trained convolutional neural net, against the respective contamination indication, for instance as illustrated in FIG. 10, or for instance as a single composite three-dimensional channel.

In some embodiments, the method further comprises constructing, for each respective training subject in the plurality of training subjects, a third channel comprising a third plurality of parameters, where each respective parameter in the third plurality of parameters may be an error statistic associated with a corresponding single nucleotide variant in the set of single nucleotide variants.

In some embodiments, the single nucleotide variant error statistic comprises a site-specific error rate (e.g., for the particular site of the SNV). In some embodiments, the site-specific error rate is between 0 and 1. In some embodiments, the single nucleotide variant error statistic comprises a trinucleotide context error rate. In some embodiments, the trinucleotide context error rate is between 0 and 1. Thus, in some embodiments, for a given training subject for a given single nucleotide variant, a first parameter in the first plurality of parameters (associated with the first channel) may encode a single nucleotide variant allele frequency of a single nucleotide variant corresponding to the first parameter, while a corresponding second parameter in the second plurality of parameters (associated with the second channel) may encode a sequencing depth for this single nucleotide variant, while a corresponding third parameter in the third plurality of parameters (associated with the third channel) may encode an error statistic associated with the sequencing of this single nucleotide variant.

In some embodiments, each parameter in the third plurality of parameters may uniquely correspond to a parameter in the second plurality of parameters, each parameter in the second plurality of parameters may uniquely correspond to a parameter in the first plurality of parameters, and each parameter in the first plurality of parameters may uniquely correspond to a single nucleotide variant in the set of single nucleotide variants.

In one example, for a particular single nucleotide variant in the set of single nucleotide variants for a particular training subject, a parameter in the first channel encodes the single nucleotide variant allele frequency of the particular single nucleotide variant, a parameter in the second channel encodes the sequencing depth for the sequencing data supporting the single nucleotide variant allele frequency of the particular single nucleotide variant in the sequencing data obtained for the particular training subject, while a parameter in the third channel encodes an error statistic associated with the sequencing of this particular single nucleotide variant.

In some embodiments, the second and third channel are each layered next to the first channel thus forming a composite channel. This may be illustrated as channels 142-1, 142-2, and 142-3 of FIG. 5. For instance, in some embodiments, this composite channel may have the form of a three dimensional matrix with order N×M×3, where N (x-axis of FIG. 5) may be the number of variants in the set of single nucleotide variants, and M (y-axis of FIG. 5) may range from a first scalar value to a second scalar value associated with the observed values for the channels (e.g., the single nucleotide variant allele frequency, sequencing depth, or sequencing error statistic), and the number 3 (z-axis of FIG. 5) may represent the three respective channels. The three dimensional matrix with order N×M×3 thus may define three two-dimensional arrays, one for each of the three channels. In the first two-dimensional array, the scalar values may represent observed variant allele frequency of the first channel. In the second two-dimensional array, the scalar values may represent the observed sequencing depths of the second channel. In the third two-dimensional array, the scalar values may represent the observed error statistic of the third channel. In such embodiments, this composite channel may be inputted into the convolutional neural network. Thus, referring to FIG. 10, in some embodiments, there may be a single stack of layers in the convolutional neural network (e.g., for the composite channel) and no other channels or stack of layers. In other words, in such embodiments, first channel 142-1 may be a single composite channel. In other embodiments, the second and third channels may not be layered next to the first channel but rather may be independently inputted into the convolutional neural network. In such embodiments, the second channel may have a first dimension that represents the genomic position (of the corresponding single nucleotide variant) and a second dimension that represents the number of fragments observed in the training subject from which the variant allele frequency (of the corresponding single nucleotide variant) is drawn (e.g., single nucleotide variant depth of each respective single nucleotide variant in the set of single nucleotide variants). Similarly, in such embodiments, the third channel may have a first dimension that may represent the genomic position (of the corresponding single nucleotide variant) and a second dimension that may represent the error statistic associated with the sequencing of each single nucleotide variant. Thus, referring to FIG. 10, in some embodiments, there may be three stacks of layers (e.g., one for the first two-dimensional channel 142-1, one for the second two-dimensional channel 142-2, and one for the third two-dimensional channel 142-3). Thus, there are a number of different ways in which the variant allele frequency for a set of SNVs, as well as other metrics for the SNVs, such as sequencing depth, error statistics, and loss of heterozygosity may be presented to a untrained or partially trained convolutional neural network.

In some embodiments, training an untrained or partially trained convolutional neural net further comprises using, for each respective training subject in the plurality of training subjects, at least the corresponding third channel of the respective training subject, as input to the untrained or partially trained convolutional neural net, against the respective contamination indication. That is, in some embodiments, the first and third channels may be concurrently inputted into the untrained or partially trained convolutional neural net either stacked on each other as illustrated in FIG. 5, or independently as illustrated in FIG. 10. In other embodiments, the first, second and third channels may be concurrently inputted into the untrained or partially trained convolutional neural net.

In some embodiments, the method further comprises constructing, for each respective training subject in the plurality of training subjects, a corresponding fourth channel comprising a fourth plurality of parameters. The fourth plurality of parameters includes a respective parameter indicating a loss of heterozygosity for each respective single nucleotide variant in the set of single nucleotide variants. In some embodiments, the respective parameter indicating a loss of heterozygosity is a binary parameter (e.g., 0 for heterozygosity and 1 for loss of heterozygosity). Many of the chromosomes within somatic cells of individuals are paired, allowing for SNP locations to be potentially heterozygous. However, one parental copy of a region can sometimes be lost, which may result in the region having just one copy. The single copy cannot be heterozygous at SNP locations and therefore the region shows loss of heterozygosity (LOH). Loss of heterozygosity due to loss of one parental copy in a region is also called hemizygosity in that region. Thus, the fourth channel can be used to flag any single nucleotide variants in the set of set of single nucleotide variants for which such loss of heterozygosity has been incurred in a respective training subject.

In some embodiments, training an untrained or partially trained convolutional neural net further comprises using, for each respective training subject in the plurality of training subjects, at least the corresponding fourth channel of the respective training subject, as input to the untrained or partially trained convolutional neural net, against the respective contamination indication (label) for the respective training subject. That is, in some embodiments, the first and fourth channels may be concurrently inputted into the untrained or partially trained convolutional neural net either stacked on each other as illustrated in FIG. 5, or independent of each other as illustrated in FIG. 10. In other embodiments, the first, second and fourth channels may be concurrently inputted into the untrained or partially trained convolutional neural net either stacked on each other as illustrated in FIG. 5, or independent of each other as illustrated in FIG. 10. In other embodiments, the first, third and fourth channels may be concurrently inputted into the untrained or partially trained convolutional neural net either stacked on each other as illustrated in FIG. 5, or independent of each other as illustrated in FIG. 10. In other embodiments, the first, second, third and fourth channels may be concurrently inputted into the untrained or partially trained convolutional neural either stacked on each other as illustrated in FIG. 5, or independent of each other as illustrated in FIG. 10.

In some embodiments, one or more additional channels are constructed for the set of SNVs in the reference genome. In some embodiments, the corresponding set of SNVs is ordered in each respective channel in accordance with a respective position of each single nucleotide variant in the corresponding set of single-nucleotide variants in the reference genome. In some embodiments, each single nucleic variant in the corresponding set of single nucleotide variants in each channel may be fixed to a respective column or row of pixels in the respective channel, or to a particular Cartesian coordinate value (x,y) within the channel. In some embodiments, where the channels are combined into a composite channel, each single nucleic variant in the corresponding set of single nucleotide variants in each component channel within the composite channel may be fixed to a respective column or row of voxels in the respective channel, or to a particular voxel in the respective column or row.

The method may continue by training an untrained or partially trained convolutional neural net using, for each respective training subject in the plurality of training subjects, at least the corresponding first channel of the respective training subject, as input to the untrained or partially trained convolutional neural net, against the respective contamination indication for the respective training subject. In some embodiments, the training thereby provides the trained convolutional neural net that is able to perform contamination analysis on test subjects for which the contamination status may not be known.

In some embodiments, training the untrained or partially trained convolutional neural net includes modifying or replacing one or more convolutional layers of the untrained or partially trained convolutional neural net (e.g., an image analysis classification layer) with one or more contamination analysis convolutional layers (e.g., a contaminated vs. non-contaminated binary classification layer). In some embodiments, training the untrained or partially trained convolutional neural net includes modifying or replacing one or more classification layers of the untrained or partially trained convolutional neural net with a contamination classification layer.

In some embodiments, training the untrained or partially trained convolutional neural net includes stratifying, on a random basis, the plurality of training subjects into a plurality of groups based on any combination of conditions (e.g., cancer condition, tumor fraction, age, gender, etc.). In some embodiments, the plurality of training subjects are stratified into a plurality of groups completely randomly (e.g., ignoring cancer condition, tumor fraction, age, gender, etc.). In some embodiments, the training further comprises using a first group in the plurality of groups as a training group and the remainder of the plurality of groups as test groups to train the untrained or partially trained convolutional neural net against the training group (e.g., a randomly selected 20% of the plurality of training subjects are included in the first group and the other 80% of the plurality of training subjects are included in the test groups). In some embodiments, the training further comprises repeating using the groups for training and test groups, for each group in the plurality of groups, so that each group in the plurality of groups is used as the training group in an iteration. In some embodiments, the training group comprises at least 5%, at least 10%, at least 15%, at least 20%, at least 25%, or at least 30% of the training subjects in the plurality of training subjects. In some embodiments, the training group consists of at most 5%, at most 10%, at most 15%, at most 20%, at most 25%, or at most 30% of the training subjects in the plurality of training subjects. In some embodiments, the training further comprises repeating the stratifying, using groups and repeating iterations until a classifier performance criterion is satisfied.

In some such embodiments, the cancer condition is a tissue of origin and each subject in the cohort of subjects is labeled with a tissue of origin. In some further such embodiments, the cohort includes subjects that have an anorectal cancer, a bladder cancer, a breast cancer, a cervical cancer, a colorectal cancer, a head and neck cancer, a hepatobiliary cancer, an endometrial cancer, a kidney cancer, a leukemia, a liver cancer, a lung cancer, a lymphoid neoplasm, a melanoma, a multiple myeloma, a myeloid neoplasm, an ovary cancer, a non-Hodgkin lymphoma, a pancreatic cancer, a prostate cancer, a renal cancer, a thyroid cancer, an upper gastrointestinal tract cancer, a urothelial carcinoma, or a uterine cancer.

In some such embodiments, the cancer condition is a stage of an anorectal cancer, a stage of bladder cancer, a stage of breast cancer, a stage of cervical cancer, a stage of colorectal cancer, a stage of head and neck cancer, a stage of hepatobiliary cancer, a stage of endometrial cancer, a stage of kidney cancer, a stage of leukemia, a stage of liver cancer, a stage of lung cancer, a stage of lymphoid neoplasm, a stage of melanoma, a stage of multiple myeloma, a stage of myeloid neoplasm, a stage of ovary cancer, a stage of non-Hodgkin lymphoma, a stage of pancreatic cancer, a stage of prostate cancer, a stage of renal cancer, a stage of thyroid cancer, a stage of upper gastrointestinal tract cancer, a stage of urothelial carcinoma, or a stage of uterine cancer. In some such embodiments, the cancer condition is whether or not a subject has cancer and the stratifying the cohort of subjects ensures that each group in the plurality groups has equal numbers of subjects that have cancer and that do not have cancer.

In some embodiments, the classifier performance criterion is satisfied when classifier performance is about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 98.5, 99, 99.5, 99.6, 99.7, 99.8, or 99.9 percent sensitivity (accuracy) at about 80, 80, 81, 82, 83, 84, 85, 86, 87, 88, 89, 90, 91, 92, 93, 94, 95, 96, 97, 98, 98.5, 99, 99.1, 99.2, 99.3, 99.4, 99.5, 99.6, 99.7, 99.8, or 99.9 percent specificity across the cohort of subjects.

Figure 8A:
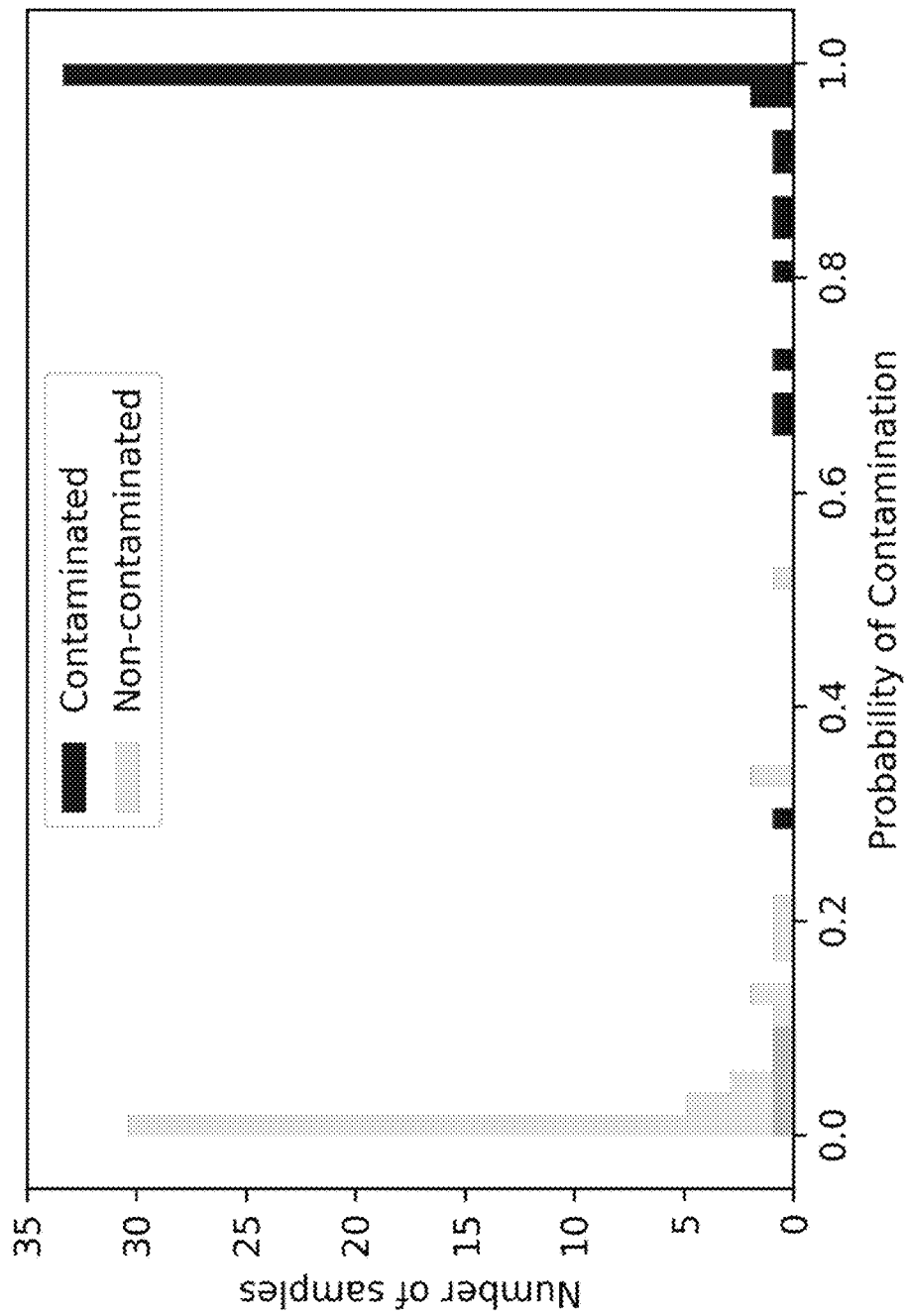
FIGS. 8A and 8B illustrate examples of contamination determination, when training samples are correctly or incorrectly labeled, in accordance with some embodiments of the present disclosure.
Figure 8B:
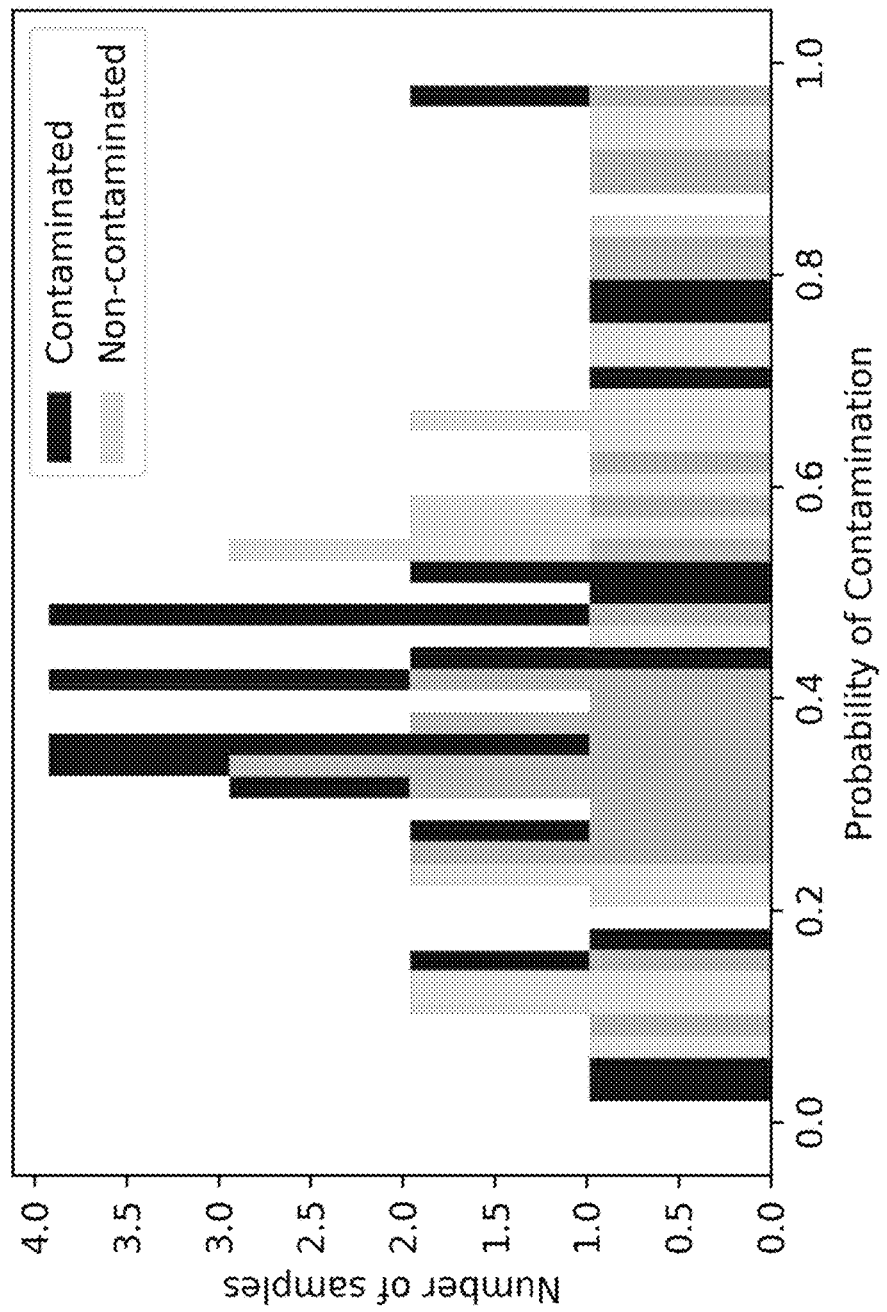

FIGS. 8A and 8B provides an example of classifier validation. The graphs in FIG. 8 illustrate classifier output for training samples that were labeled corrected as contaminated or not contaminated (e.g., panel 802) or incorrectly (e.g., panel 804). As seen in panel 802, nearly all of the correctly labeled samples are accurately categorized by the classifier (e.g., as evidenced by the two peaks at 0 and 1.0). Panel 804, in contrast, illustrates the difficulties for the classifier in accurately identifying incorrectly labeled training samples (e.g., the samples are all muddled together in the middle and there are no peaks at 0 and 1).

In some embodiments, the untrained or partially trained convolutional neural net comprises at least one of i) one or more convolutional layers, where each convolutional layer comprises one or more filters (e.g., kernels), a respective size (e.g., n×n), and a respective stride, ii) one or more pooling layers, where each pooling layer comprises a respective size and a respective stride, iii) one or more fully connected layers, where each fully connected layer comprises a plurality of nodes, and iv) one or more of a classifying layer and/or a hidden layer.

In some embodiments, the untrained or partially trained classifier comprises an input layer of respective training data, where the size of training data (e.g., the corresponding first channel for each respective training subject in the plurality of training subjects) comprises a first number of dimensions (e.g., 250×250, 1024×768, etc.). In some embodiments, the respective training data is reshaped for analysis (e.g., converted from a three-dimensional matrix to a one-dimensional vector).

In some embodiments, the untrained or partially trained classifier comprises one or more convolutional layers, where the respective parameters for each convolutional layer are filters. Each filter has a corresponding height and width. In typical embodiments, a respective filter is smaller than the input image to the corresponding convolutional layer.

In some embodiments, the untrained or partially trained classifier comprises one or more pooling layers (e.g., downsampling layers) that are used to reduce the number of parameters (e.g., to reduce the computational complexity). In some embodiments, a pooling layer is interspersed between two other layers (e.g., two convolutional layers).

In some embodiments, a respective stride for a corresponding convolutional or pooling layer is at least 1, at least 2, at least 3, at least 4, at least 5, at least 6, at least 7, at least 8, at least 9, or at least 10. In some embodiments, the respective stride for a corresponding convolutional or polling layer is at most 10, 9, 8, 7, 6, 5, 4, 3, 2, or 1.

In some embodiments, a respective size for a corresponding convolutional or pooling layer is a respective matrix (n×n) of pixels. In some embodiments, n is at least 1, at least 2, at least 3, at least 4, at least 5, at least 6, at least 7, at least 8, at least 9, or at least 10. In some embodiments, n is at most 10, 9, 8, 7, 6, 5, 4, 3, 2, or 1. In some embodiments, a size of a corresponding pooling layer is smaller (e.g., has a smaller n) than the size of an upstream convolutional or pooling layer.

In some embodiments, the untrained or partially trained classifier comprises one or more fully connected embedding layers that each comprises a corresponding set of weights. In some embodiments, a respective fully connected embedding layer directly or indirectly receives an output of the input layer. In some embodiments, an output of the respective embedding layer comprises a second number of dimensions different from the first number of dimensions. That is, in some embodiments, the second number of dimensions is less than the first number of dimensions.

In some embodiments, the untrained or partially trained classifier comprises at least one hidden layer. Hidden layers are located between input and output layers (e.g., to capture additional complexity). In some embodiments, where there is a plurality of hidden layers, each hidden layer may have a same respective number of neurons.

In some embodiments, the untrained or partially trained classifier comprises one or more classifying layers (e.g., output layers). In some embodiments, a classifying layer provides binary output (e.g., decides between two options such as contaminated and non-contaminated). In some embodiments, a classifying layer provides multiclass output (e.g., provides a predicted level of contamination for a sample).

In some embodiments, the untrained or partially trained convolutional neural net comprises a corresponding plurality of inputs, where each input in the corresponding plurality of inputs is for a parameter in the first plurality of parameters (e.g., the single nucleotide variant allele frequency of each respective single nucleotide variant in the set of single nucleotide variants observed for a respective subject), a corresponding first hidden layer comprising a corresponding plurality of hidden neurons, where each hidden neuron in the corresponding plurality of hidden neurons (i) is fully connected to each input in the plurality of inputs, (ii) is associated with a first activation function type, and (iii) is associated with a corresponding weight in a plurality of weights for the untrained or partially trained convolutional neural net, and one or more corresponding neural network outputs, where each respective neural network output in the corresponding one or more neural network outputs (i) directly or indirectly receives, as input, an output of each hidden neuron in the corresponding plurality of hidden neurons, and (ii) is associated with a second activation function type. In some such embodiments, the untrained or partially trained convolutional neural net is a fully connected network. In some such embodiments, the first activation function type and the second activation function type are the same or different and are each one of tanh, sigmoid, softmax, Gaussian, Boltzmann-weighted averaging, absolute value, linear, rectified linear unit (ReLU), bounded rectified linear, soft rectified linear, parameterized rectified linear, average, max, min, sign, square, square root, multiquadric, inverse quadratic, inverse multiquadric, polyharmonic spline, or thin-plate spline. In some embodiments, the untrained or partially trained convolutional neural net is trained using a regularization on the corresponding weight of each hidden neuron in the plurality of hidden neurons. In some embodiments, the regularization includes an L1 or L2 penalty.

In some embodiments, the training of the untrained or partially trained convolutional neural net may further be characterized by one or more hyperparameters (e.g., one or more values that may be tuned during training). In some embodiments, the hyperparameter values are tuned (e.g., adjusted) during training. In some embodiments, the hyperparameter values are determined based on the specific elements of the assay (e.g. sample size, sample type, method of methylation sequencing, fragment quality, methylation patterns, among others). In some embodiments, the hyperparameter values are determined using experimental optimization. In some embodiments, the hyperparameter values are assigned based on prior template or default values.

In some embodiments, a respective hyperparameter of the one or more hyperparameters comprises a number of training epochs used in leave-one-out cross-validation of the training set. In some embodiments, the number of epochs is at least 1, at least 2, at least 3, at least 4, at least 5, at least 6, at least 7, at least 8, at least 9, or at least 10. In some embodiments, the number of epochs is at most 10, 9, 8, 7, 6, 5, 4, 3, 2, or 1.

In some embodiments, a respective hyperparameter of the one or more hyperparameters comprises a batch size. In some embodiments, the batch size is at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 training subjects selected from the plurality of training subjects. In some embodiments, the batch size is at most 100, 95, 90, 85, 80, 75, 70, 65, 60, 55, 50, 45, 40, 35, 30, 25, 20, 15, 10, 5 or less training subjects selected from the plurality of training subjects. In some embodiments, the batch size is a percentage of the plurality of training subjects (e.g., at least 5%, at least 10%, at least 15%, at least 20%, at least 25%, at least 30% or at least 35% of the plurality of training subjects).

In some embodiments, a respective hyperparameter of the one or more hyperparameters comprises a learning rate. In some embodiments, the learning rate is at least 0.1, at least 0.2, at least 0.3, at least 0.4, at least 0.5, at least 0.6, at least 0.7, at least 0.8, at least 0.9, or at least 1. In some embodiments, the learning rate is at most 1, 0.9, 0.8, 0.7, 0.6, 0.5, 0.4, 0.3, 0.2, 0.1 or less. In some embodiments, the learning rate further comprises a learning rate decay (e.g., a reduction in the learning rate over one or more epochs). For example, a learning decay rate could be a reduction in the learning rate of 0.5 over 5 epochs or a reduction of 0.1 over 20 epochs). Tuning the learning rate can achieve successful classification. For example, a low learning rate provides linear improvement to the learning over one or more epochs (thus using a high number of epochs to achieve accurate classification), while a high learning rate introduces chaos into training and can prevent optimization of the learning.

In some embodiments, a respective hyperparameter of the one or more hyperparameters comprises momentum. In some embodiments, momentum is set to at least 0.1, at least 0.2, at least 0.3, at least 0.4, at least 0.5, at least 0.6, at least 0.7, at least 0.8, at least 0.9, at least, 0.95, or at least 0.99. In some embodiments, momentum is set to at most 0.99, 0.95, 0.9, 0.8, 0.7, 0.6, 0.5, 0.4, 0.3, 0.2, 0.1 or less. In some embodiments, momentum is initially set to at least 0.5 and iterated to 0.99 over one or more epochs. In some embodiments, the momentum hyperparameter is an optimization that serves to control the variance rate (e.g., by altering stride distance). In some embodiments, the one or more hyperparameters further include regularization strength (e.g., L2 weight penalty, dropout rate, etc.).

In some embodiments, the untrained or partially trained neural net comprises a multilayer neural net, a deep convolutional neural net, a visual geometry convolutional neural net, or a combination thereof.

In some embodiments, the untrained or partially trained convolutional neural net may be based upon LeNet, AlexNet, VGGNet 16, GoogLeNet (e.g., Inception Network), or ResNet. Each of these specific CNNs is designed for use on image data. In some embodiments, any CNN designed to analyze image data can be used as the untrained or partially training convolutional neural net. However, in some embodiments the multi-categorical classification layers, which may have more than 1000 classifications, may be replaced with a contamination analysis classification layer (e.g., a binary contaminated versus non-contaminated binary classification layer). In some embodiments, the multi-categorical classification layers may be replaced with a plurality of non-contaminated binary classification layers.

LeNet can be one type of CNN, and variations have been developed for use with image data. In some embodiments, LeNet can comprise at least one convolutional layer, at least one pooling layer, and at least one fully-connected layer. In some embodiments, LeNet comprises a first convolutional layer, a first pooling layer (e.g., a sub-sampling layer), a second convolutional layer, a second pooling layer, a first fully-connected layer, a second fully-connected layer, and a classification (e.g., output) layer.

AlexNet can be a GPU-enabled CNN for image recognition. In some embodiments, AlexNet can comprise at least eight convolutional, pooling, and fully-connected layers. In some embodiments, AlexNet includes five convolutional layers and three fully-connected layers.

The goal of VGGNet can be used to reduce the number of parameters. In some embodiments, VGGNet comprises 13 convolutional layers, 5 max-pooling layers, 2 fully-connected layers, and a classifying layer. In some embodiments, VGGNet alternates at least two convolutional layers with a pooling layer.

GoogLeNet can use dimensionality reduction initially to reduce computation usage, which also helps to prevent overfitting. GoogLeNet comprises fewer than 30 layers.

ResNet can be a deep network that includes a high number of layers (e.g., at least 25 layers, at least 50 layers, at least 100 layers, at least 150 layers, at least 200 layers, at least 300 layers, at least 400 layers, at least 500 layers, at least 750 layers, at least 1000 layers, at least 200 layers, at least 3000 layers, at least 4000 layers or at least 5000 layers) and provide for skipping of one or more layers. The possibility of skipping over some of the layers can keep the performance of the CNN from degrading too much. In some embodiments, ResNet can comprise at least 1000 layers.

In some embodiments, the method further comprises determining a contamination status for a biological sample of a test subject of a species. In some embodiments, determining the contamination status comprises: obtaining, in electronic format, a test subject dataset comprising i) a corresponding variant allele frequency of each respective single nucleotide variant in a subject plurality of single nucleotide variants, i) constructing a first channel of the test subject (e.g., represented as an image) comprising a corresponding set of single-nucleotide variants in the reference genome, each respective single nucleotide variant corresponding to an independent location in the reference genome, and iii) applying the first channel of the test subject to the trained computational neural net, thereby obtaining a test contamination indication for the biological sample of the test subject.

In some embodiments, each variant allele frequency is determined by sequencing one or more nucleic acids in the biological sample obtained from the test subject. In some embodiments, the first channel of the test subject comprises a first plurality of parameters, where the first plurality of parameters includes a respective parameter for a single nucleotide variant allele frequency of each respective single nucleotide variant in the set of single nucleotide variants.

In some embodiments, determining the contamination status for the biological sample of the test subject comprises identifying the biological sample as either contaminated or not. In some embodiments, the determination of contamination comprises providing an estimation of contamination percentage for the biological sample of the subject (e.g., less than 0.001% contamination, less than 0.003% contamination, less than 0.005% contamination, less than 0.01% contamination, less than 0.05% contamination, less than 0.1% contamination, less than 0.25% contamination, less than 0.5% contamination, less than 1% contamination, less than 2% contamination, less than 5% contamination, less than 10% contamination, less than 20% contamination, more than 0.001% contamination, more than 0.003% contamination, more than 0.005% contamination, more than 0.01% contamination, more than 0.05% contamination, more than 0.1% contamination, more than 0.25% contamination, more than 0.5% contamination, more than 1% contamination, more than 2% contamination, more than 5% contamination, more than 10% contamination, or more than 20% contamination).

In some embodiments, the test subject sample is determined to be contaminated when the test contamination indication satisfies a contamination threshold. In some embodiments, the contamination threshold is at least 5%, at least 10%, at least 20%, at least 30%, at least 40%, at least 50%, at least 60%, or at least 70%. In some embodiments, the contamination threshold is at most 70%, 60%, 50%, 40%, 30%, 20%, 10% or less. In some embodiments the contamination threshold is 0.001% contamination or less, 0.003% contamination or less, 0.005% contamination or less, 0.01% contamination or less, 0.05% contamination or less, 0.1% contamination or less, 0.25% contamination or less, 0.5% contamination or less, 1% contamination or less, 2% contamination or less, 5% contamination or less, 10% contamination or less, 20% contamination or less. In some embodiments the contamination threshold is 0.001% contamination or more, 0.003% contamination or more, 0.005% contamination or more, 0.01% contamination or more, 0.05% contamination or more, 0.1% contamination or more, 0.25% contamination or more, 0.5% contamination or more, 1% contamination or more, 2% contamination or more, 5% contamination or more, 10% contamination or more, 20% contamination or more.

In some embodiments, the method further comprises determining a contamination confidence value for the contamination indication for the biological sample of the test subject.

In some embodiments, the method further comprises pre-training the untrained or partially trained convolutional neural net. In some embodiments, the pre-training comprises i) obtaining, in electronic format, a pre-training dataset, where the pre-training dataset comprises, for each respective pre-training object in a plurality of pre-training objects, a corresponding image, and a respective pre-training label, and training the untrained or partially trained convolutional neural net using, for each respective pre-training object in the plurality of pre-training objects, at least the corresponding image of the respective pre-training object as input to the untrained or partially trained convolutional neural net against the respective pre-training label.

In some embodiments, the pre-training uses a plurality of images from the ImageNet dataset. ImageNet can comprise millions of labeled images from different categories (e.g., not necessarily related to medical images). In some embodiments, any image files (e.g., any labeled image files) can be used for the pre-training. After the pre-training on random image data, a final classification layer of the untrained or partially trained classifier can be trained on biological sample image data for contamination detection. In some embodiments, the images may be any form of two-dimensional RGB pixelated images.

In some embodiments, the pre-training can be performed as described in U.S. Provisional Patent Application 62/948,129, entitled "Cancer classification using patch convolutional neural networks," filed Dec. 13, 2019, which is hereby incorporated herein by reference in its entirety.

Figure 13:
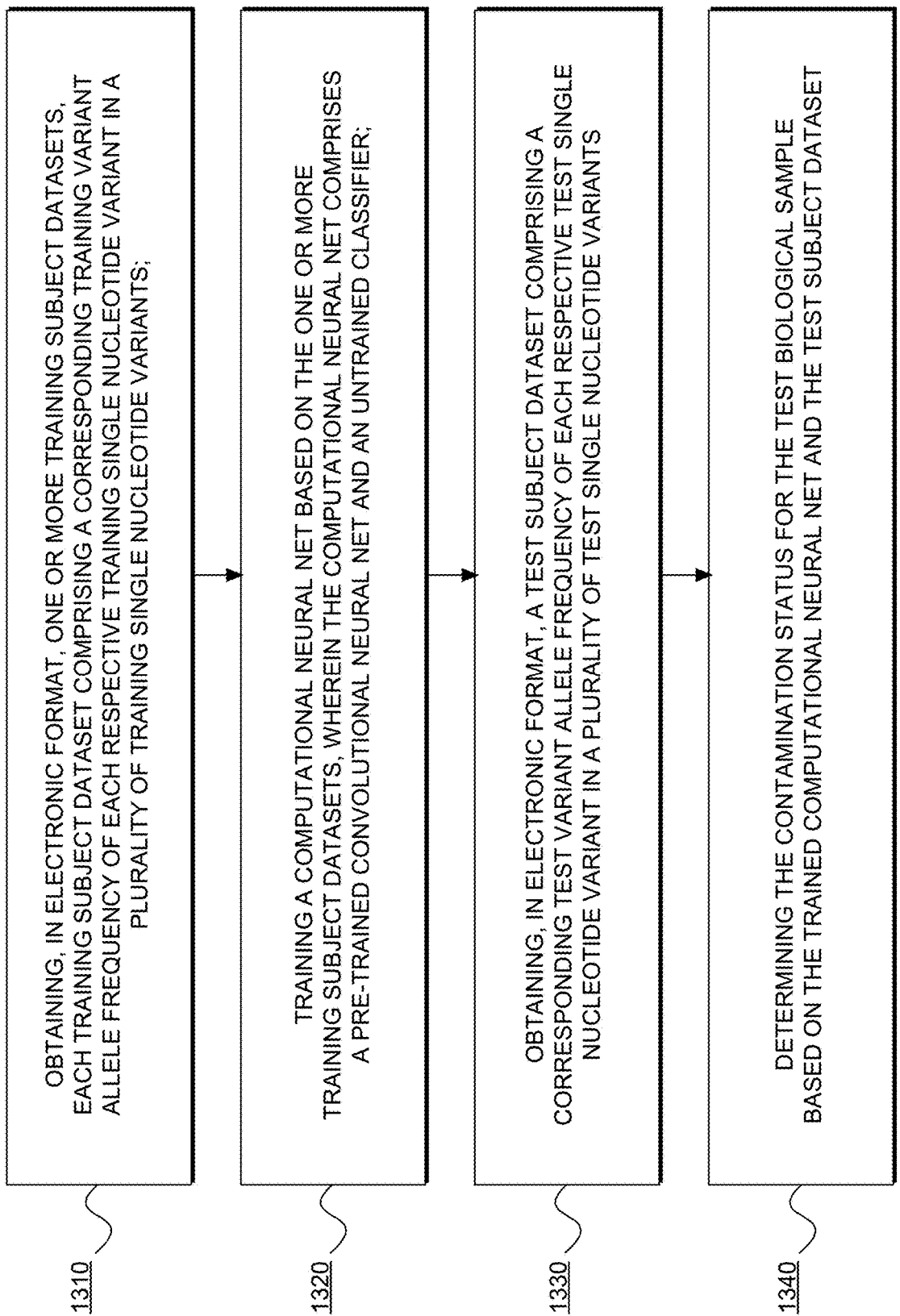
FIG. 13 illustrates an example flowchart of a method of performing contamination analysis, in accordance with some embodiments of the present disclosure.

FIG. 13 depicts another exemplary flowchart describing a method of determining a contamination status of a test biological sample obtained from a test subject. The method can be performed by the environment 100 and/or the processing system 160 disclosed herein.

Step 1310 comprises obtaining, in electronic format, one or more training subject datasets. The training subject dataset can comprise a corresponding training variant allele frequency of each respective training single nucleotide variant in a plurality of training single nucleotide variants. The training subject datasets can be used to train a computational neural net. Each training variant allele frequency in the plurality of training single nucleotide variants can be determined by sequencing one or more nucleic acids in one or more training biological samples. The plurality of training single nucleotide variants can comprise at least 10, 20, 30, 40, 50, 60, 70, 80, 90, 100, 150, 200, 250, 200 or more training single nucleotide variants. The plurality of training single nucleotide variants can comprise at most 300, 250, 200, 150, 100, 90, 80, 70, 60, 50, 40, 30, 20, 10 or less training single nucleotide variants. The training single nucleotide variants can be used to train a computational neural net.

Step 1320 comprises training a computational neural net based on the one or more training subject datasets. The computational neural net can comprise a pre-trained convolutional neural net and an untrained classifier. Details of the computational neural net, the pre-trained convolutional neural net, the untrained classifier, and how to train the computational neural net are described elsewhere herein.

Step 1330 comprises obtaining, in electronic format, a test subject dataset comprising a corresponding test variant allele frequency of each respective test single nucleotide variant in a plurality of test single nucleotide variants. Each test variant allele frequency in the plurality of test single nucleotide variants can be determined by sequencing one or more nucleic acids in the test biological sample. The plurality of test single nucleotide variants can comprise 10, 20, 30, 40, 50, 60, 70, 80, 90, 100, 150, 200, 250, 300, or more test single nucleotide variants. The plurality of test single nucleotide variants can comprise at most 300, 250, 200, 150, 100, 90, 80, 70, 60, 50, 40, 30, 20, 10 or less test single nucleotide variants.

Step 1340 comprises determining the contamination status for the test biological sample based on the trained computational neural net and the test subject dataset. The contamination status can comprise the test biological sample is either contaminated or not. In some embodiments, the contamination status comprises an estimation of contamination percentage for the biological sample of the subject (e.g., less than 0.001% contamination, less than 0.003% contamination, less than 0.005% contamination, less than 0.01% contamination, less than 0.05% contamination, less than 0.1% contamination, less than 0.25% contamination, less than 0.5% contamination, less than 1% contamination, less than 2% contamination, less than 5% contamination, less than 10% contamination, less than 20% contamination, more than 0.001% contamination, more than 0.003% contamination, more than 0.005% contamination, more than 0.01% contamination, more than 0.05% contamination, more than 0.1% contamination, more than 0.25% contamination, more than 0.5% contamination, more than 1% contamination, more than 2% contamination, more than 5% contamination, more than 10% contamination, or more than 20% contamination). The determining the contamination status comprises inputting the test subject dataset into the computational neural net to calculate the estimation of contamination percentage for the biological sample of the test subject.

FIG. 14 shows an exemplary computer system 1401 that is programmed or otherwise configured to determine a disease condition of a test subject of a species. The computer system 1401 can implement and/or regulate various aspects of the methods provided in the present disclosure, such as, for example, performing the method of determining a cancer condition of a test subject as described herein, performing various steps of the bioinformatics analyses of training dataset and testing dataset as described herein, integrating data collection, analysis and result reporting, and data management. The computer system 1401 can be an electronic device of a user or a computer system that is remotely located with respect to the electronic device. The electronic device can be a mobile electronic device.

The computer system 1401 can include a central processing unit (CPU, also "processor" and "computer processor" herein) 1405, which can be a single core or multi core processor, or a plurality of processors for parallel processing. The computer system 1401 can also include memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 can be in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases can be a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user (e.g., a Smart phone installed with application that receives and displays results of sample analysis sent from the computer system 1401). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that include a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that includes a user interface (UI) 1440 for providing, for example, results of sample analysis, such as, but not limited to graphic showings of the stage of processing the input sequencing data, output sequencing data, and further classification of pathology (e.g., type of disease or cancer and level of cancer). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can perform any step of the methods described here.

ADDITIONAL EMBODIMENTS

Example 1—Obtaining a Plurality of Sequence Reads

Figure 11:
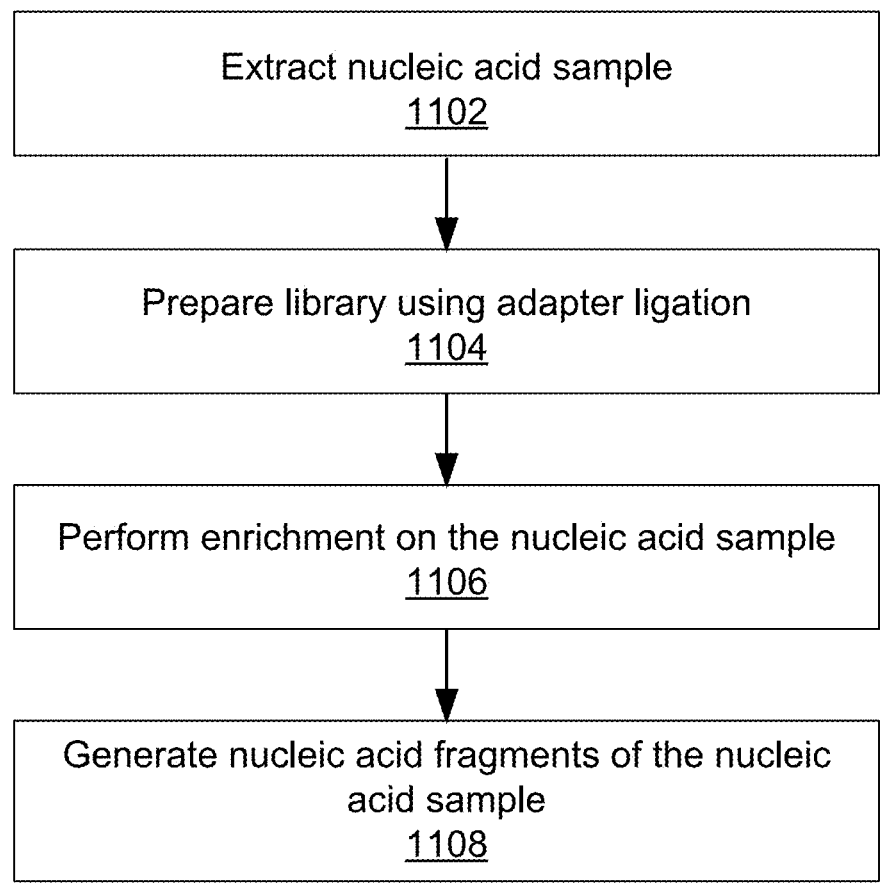
FIG. 11 illustrates a flowchart of a method for preparing a nucleic acid sample for sequencing in accordance with some embodiments of the present disclosure.

FIG. 11 is a flowchart of method 1100 for preparing a nucleic acid sample for sequencing according to one embodiment. The method 1100 includes, but is not limited to, the following steps. For example, any step of method

1100 may comprise a quantitation sub-step for quality control or other laboratory assay procedures known to one skilled in the art.

In block 1102, a nucleic acid sample (DNA or RNA) is extracted from a subject. The sample may be any subset of the human genome, including the whole genome. The sample may be extracted from a subject known to have or suspected of having cancer. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may use surgery. The extracted sample may comprise cfDNA and/or ctDNA. For healthy individuals, the human body may naturally clear out cfDNA and other cellular debris. If a subject has a cancer or disease, ctDNA in an extracted sample may be present at a detectable level for diagnosis.

In block 1104, a sequencing library is prepared. During library preparation, unique molecular identifiers (UMI) are added to the nucleic acid molecules (e.g., DNA molecules) through adapter ligation. The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment. This provides a way to identify sequence reads that came from the same original fragment in downstream analysis.

In block 1106, targeted DNA sequences are enriched from the library. During enrichment, hybridization probes (also referred to herein as "probes") are used to target, and pull down, nucleic acid fragments informative for the presence or absence of cancer (or disease), cancer status, or a cancer classification (e.g., cancer class or tissue of origin). For a given workflow, the probes may be designed to anneal (or hybridize) to a target (complementary) strand of DNA. The target strand may be the "positive" strand (e.g., the strand transcribed into mRNA, and subsequently translated into a protein) or the complementary "negative" strand. The probes may range in length from 10s, 100s, or 1000s of base pairs. In one embodiment, the probes are designed based on a methylation site panel. In one embodiment, the probes are designed based on a panel of targeted genes to analyze particular mutations or target regions of the genome (e.g., of the human or another organism) that are suspected to correspond to certain cancers or other types of diseases. Moreover, the probes may cover overlapping portions of a target region. In block 1108, these probes are used to general sequence reads of the nucleic acid sample.

Figure 6:
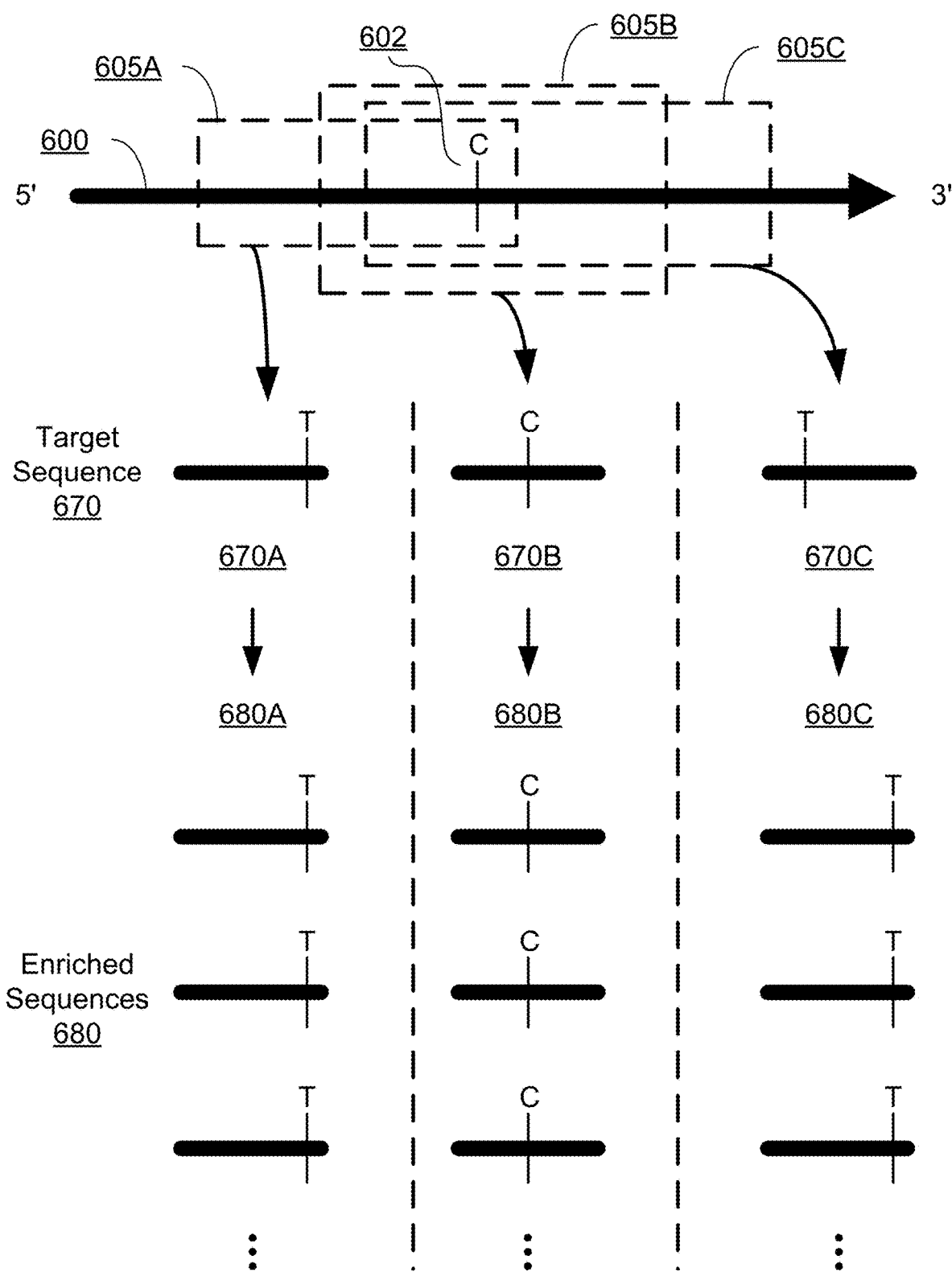
FIG. 6 illustrates a graphical representation of the process for obtaining sequence reads in accordance with some embodiments of the present disclosure

FIG. 6 is a graphical representation of the process for obtaining sequence reads according to one embodiment. FIG. 6 depicts one example of a nucleic acid segment 600 from the sample. Here, the nucleic acid segment 600 can be a single-stranded nucleic acid segment, such as a single-stranded. In some embodiments, the nucleic acid segment 600 is a double-stranded cfDNA segment. The illustrated example depicts three regions 605A, 605B, and 605C of the nucleic acid segment that can be targeted by different probes. Specifically, each of the three regions 605A, 605B, and 605C includes an overlapping position on the nucleic acid segment 600. An example overlapping position is depicted in FIG. 6 as the cytosine ("C") nucleotide base 602.

The cytosine nucleotide base 602 is located near a first edge of region 605A, at the center of region 605B, and near a second edge of region 605C.

In some embodiments, one or more (or all) of the probes are designed based on a gene panel or methylation site panel to analyze particular mutations or target regions of the genome (e.g., of the human or another organism) that are suspected to correspond to certain cancers or other types of diseases. By using a targeted gene panel or methylation site panel rather than sequencing all expressed genes of a genome, also known as "whole-exome sequencing," the method 600 may be used to increase sequencing depth of the target regions, where depth refers to the count of the number of times a given target sequence within the sample has been sequenced. Increasing sequencing depth reduces the input amounts of the nucleic acid sample that are typically needed.

Hybridization of the nucleic acid sample 600 using one or more probes results in an understanding of a target sequence 670. As shown in FIG. 6, the target sequence 670 is the nucleotide base sequence of the region 605 that is targeted by a hybridization probe. The target sequence 670 can also be referred to as a hybridized nucleic acid fragment. For example, target sequence 670A corresponds to region 605A targeted by a first hybridization probe, target sequence 670B corresponds to region 605B targeted by a second hybridization probe, and target sequence 670C corresponds to region 605C targeted by a third hybridization probe. Given that the cytosine nucleotide base 602 is located at different locations within each region 605A-C targeted by a hybridization probe, each target sequence 670 includes a nucleotide base that corresponds to the cytosine nucleotide base 602 at a particular location on the target sequence 670.

After a hybridization step, the hybridized nucleic acid fragments are captured and may also be amplified using PCR. For example, the target sequences 670 can be enriched to obtain enriched sequences 680 that can be subsequently sequenced. In some embodiments, each enriched sequence 680 is replicated from a target sequence 670. Enriched sequences 680A and 680C that are amplified from target sequences 670A and 670C, respectively, also include the thymine nucleotide base located near the edge of each sequence read 680A or 680C. As used hereafter, the mutated nucleotide base (e.g., thymine nucleotide base) in the enriched sequence 680 that is mutated in relation to the reference allele (e.g., cytosine nucleotide base 602) is considered as the alternative allele. Additionally, each enriched sequence 680B amplified from target sequence 670B includes the cytosine nucleotide base located near or at the center of each enriched sequence 680B.

Sequence reads and fragments can be generated from the enriched DNA sequences, e.g., enriched sequences 680 shown in FIG. 6. Sequencing data may be acquired from the enriched DNA sequences by known means in the art. For example, the method 600 may include next-generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

In some embodiments, the sequence reads may be aligned to a reference genome using known methods in the art to determine the alignment position information. The alignment position information may indicate a beginning position and an end position of a region in the reference genome that corresponds to a beginning nucleotide base and end nucleotide base of a given sequence read. The alignment position information may also include sequence read length, which can be determined from the beginning position and end position. A region in the reference genome may be associated with a gene or a segment of a gene.

In some embodiments, an average sequence read length of a corresponding plurality of sequence reads obtained by the methylation sequencing for a respective fragment is between 140 and 280 nucleotides.

In various embodiments, a sequence read is comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome represent the likely location within the reference genome to which the nucleic acid fragment corresponds. An output file having SAM (sequence alignment map) format or BAM (binary) format may be generated and output for further analysis such as methylation state determination.

Example 2—Ability to Detect Cancer as a Function of cfDNA Fraction

In some embodiments, the method further comprises training a classifier to determine a cancer condition of the subject or a likelihood of the subject obtaining the cancer condition using at least tumor fraction estimation information associated with a plurality of variant calls (e.g., based at least in part on one or more respective called variants for one or more corresponding allelic positions of the subject). In some embodiments, biological samples that are determined to not be contaminated using the methods described herein are used for cancer detection analysis.

For example, in some embodiments, an untrained classifier is trained on a training set comprising one or more reference pluralities of variant calls, where each reference plurality of variant calls is associated with corresponding tumor fraction estimation information.

In some embodiments, the classifier is an unsupervised learning algorithm. One example of an unsupervised learning algorithm is cluster analysis. In some embodiments, the classifier is supervised machine learning. Nonlimiting examples of supervised learning algorithms include, but are not limited to, logistic regression, neural networks, support vector machines, Naive Bayes algorithms, nearest neighbor algorithms, random forest algorithms, decision tree algorithms, boosted trees algorithms, multinomial logistic regression algorithms, linear models, linear regression, GradientBoosting, mixture models, hidden Markov models, Gaussian NB algorithms, linear discriminant analysis, or any combinations thereof. In some embodiments, the trained classifier is a multinomial classifier algorithm (e.g., for classifying tissue of origin).

Classifiers for use in some embodiments are described in further detail in, e.g., U.S. Provisional Patent Application 62/948,129, entitled "Cancer classification using patch convolutional neural networks," filed Dec. 13, 2019, and U.S. patent application Ser. No. 16/719,902, entitled "Systems and Methods for Estimating Cell Source Fractions Using Methylation Information," filed Dec. 18, 2019, each of which is hereby incorporated herein by reference in its entirety. In some embodiments the classifier makes use of the B score classifier described in U.S. patent application Ser. No. 16/352,739, entitled "Method and System for Selecting, Managing, and Analyzing Data of High Dimensionality," filed Oct. 9, 2019, which is hereby incorporated by reference. In some embodiments, the classifier makes use of the M score classifier described in U.S. Patent Application No. 62/642,480, entitled "Methylation Fragment Anomaly Detection," filed Mar. 13, 2018, which is hereby incorporated by reference.

Neural networks. In some embodiments, the classifier is a neural network or a convolutional neural network. Neural network algorithms, also known as artificial neural networks (ANNs), can include convolutional neural network algorithms (deep learning algorithms). Neural networks can be machine learning algorithms that may be trained to map an input data set to an output data set, where the neural network comprises an interconnected group of nodes organized into multiple layers of nodes. For example, the neural network architecture may comprise at least an input layer, one or more hidden layers, and an output layer. The neural network may comprise any total number of layers, and any number of hidden layers, where the hidden layers function as trainable feature extractors that allow mapping of a set of input data to an output value or set of output values. As used herein, a deep learning algorithm (DNN) can be a neural network comprising a plurality of hidden layers, e.g., two or more hidden layers. Each layer of the neural network can comprise a number of nodes (or "neurons"). A node can receive input that comes either directly from the input data or the output of nodes in previous layers, and perform a specific operation, e.g., a summation operation. In some embodiments, a connection from an input to a node is associated with a weight (or weighting factor). In some embodiments, the node may sum up the products of all pairs of inputs, xi, and their associated weights. In some embodiments, the weighted sum is offset with a bias, b. In some embodiments, the output of a node or neuron may be gated using a threshold or activation function, f, which may be a linear or non-linear function. The activation function may be, for example, a rectified linear unit (ReLU) activation function, a Leaky ReLu activation function, or other function such as a saturating hyperbolic tangent, identity, binary step, logistic, arcTan, softsign, parametric rectified linear unit, exponential linear unit, softPlus, bent identity, softExponential, Sinusoid, Sine, Gaussian, or sigmoid function, or any combination thereof.

The weighting factors, bias values, and threshold values, or other computational parameters of the neural network, may be "taught" or "learned" in a training phase using one or more sets of training data. For example, the parameters may be trained using the input data from a training data set and a gradient descent or backward propagation method so that the output value(s) that the ANN computes are consistent with the examples included in the training data set. The parameters may be obtained from a back propagation neural network training process.

Any of a variety of neural networks may be suitable for use in analyzing product development. Examples can include, but are not limited to, feedforward neural networks, radial basis function networks, recurrent neural networks, convolutional neural networks, and the like. In some embodiments, the machine learning makes use of a pre-trained ANN or deep learning architecture. Convolutional neural networks can be used for classifying methylation patterns in accordance with the present disclosure.

Support vector machines. In some embodiments, the classifier is a support vector machine (SVM). When used for classification, SVMs separate a given set of binary labeled data with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space can correspond to a non-linear decision boundary in the input space.

Naïve Bayes algorithms. Naive Bayes classifiers can be a family of "probabilistic classifiers" based on applying Bayes' theorem with strong (naïve) independence assumptions between the features. In some embodiments, they are coupled with Kernel density estimation. In some embodiments, the classifier is a Naive Bayes algorithm.

Nearest neighbor algorithms. Nearest neighbor classifiers can be memory-based and include no classifier to be fit. Given a query point $x_0$, the k training points $x_{(r)}$, r, . . . , k closest in distance to $x_0$ can be identified and then the point $x_0$ is classified using the k nearest neighbors. Ties can be broken at random. In some embodiments, Euclidean distance in feature space is used to determine distance as:

$$d_{(i)} = \|x_{(i)} - x_{(0)}\|$$

In some embodiments, when the nearest neighbor algorithm is used, the bin values for the training set can be standardized to have mean zero and variance 1. In some embodiments, the nearest neighbor analysis is refined to address issues of unequal class priors, differential misclassification costs, and feature selection. Many of these refinements can involve some form of weighted voting for the neighbors. In some embodiments, the classifier is a nearest neighbor algorithm.

Random forest, decision tree, and boosted tree algorithms. In some embodiments, the classifier is a decision tree. Tree-based methods can partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4.5, MART, and Random Forests.

Regression. In some embodiment, a regression algorithm is used as the classifier. A regression algorithm can be any type of regression. For example, in some embodiments, the regression algorithm is logistic regression. In some embodiments, the regression algorithm is logistic regression with lasso, L2 or elastic net regularization. In some embodiments, those extracted features that have a corresponding regression coefficient that fails to satisfy a threshold value are pruned (removed from) consideration. In some embodiments, a generalization of the logistic regression model that handles multicategory responses is used as the classifier. In some embodiments, the classifier makes use of a regression model.

Linear discriminant analysis algorithms. Linear discriminant analysis (LDA), normal discriminant analysis (NDA), or discriminant function analysis can be a generalization of Fisher's linear discriminant, a method used in statistics, pattern recognition, and machine learning to find a linear combination of features that characterizes or separates two or more classes of objects or events. The resulting combination can be used as the classifier (linear classifier) in some embodiments of the present disclosure.

Mixture model. In some embodiments, the classifier is a mixture model.

Hidden Markov model. In some embodiments, in particular, those embodiments including a temporal component, the classifier is a hidden Markov model.

Clustering. In some embodiments, the classifier is an unsupervised clustering model. In some embodiments, the classifier is a supervised clustering model. The clustering problem can be described as one of finding natural groupings in a dataset. To identify natural groupings, two issues can be addressed. First, a way to measure similarity (or dissimilarity) between two samples can be determined. This metric (e.g., similarity measure) can be used to ensure that the samples in one cluster are more like one another than they are to samples in other clusters. Second, a mechanism for partitioning the data into clusters using the similarity measure can be determined. One way to begin a clustering investigation can be to define a distance function and to compute the matrix of distances between all pairs of samples in the training set. If distance is a good measure of similarity, then the distance between reference entities in the same cluster can be significantly less than the distance between the reference entities in different clusters. However, clustering may not use of a distance metric. For example, a nonmetric similarity function s(x, x') can be used to compare two vectors x and x'. s(x, x') can be a symmetric function whose value is large when x and x' are somehow "similar." Once a method for measuring "similarity" or "dissimilarity" between points in a dataset has been selected, clustering can use a criterion function that measures the clustering quality of any partition of the data. Partitions of the data set that extremize the criterion function can be used to cluster the data. Particular exemplary clustering techniques that can be used in the present disclosure can include, but are not limited to, hierarchical clustering (agglomerative clustering using a nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. In some embodiments, the clustering comprises unsupervised clustering (e.g., with no preconceived number of clusters and/or no predetermination of cluster assignments).

The A score classifier described herein can be a classifier of tumor mutational burden based on targeted sequencing analysis of nonsynonymous mutations. For example, a classification score (e.g., "A score") can be computed using logistic regression on tumor mutational burden data, where an estimate of tumor mutational burden for each individual is obtained from the targeted cfDNA assay. In some embodiments, a tumor mutational burden can be estimated as the total number of variants per individual that are: called as candidate variants in the cfDNA, passed noise-modeling and joint-calling, and/or found as nonsynonymous in any gene annotation overlapping the variants. The tumor mutational burden numbers of a training set can be fed into a penalized logistic regression classifier to determine cutoffs at which 95% specificity is achieved using cross-validation.

The B score classifier is described in U.S. Patent Publication No. 62/642,461, filed 62/642,461, which is hereby incorporated by reference. In accordance with the B score method, a first set of sequence reads of nucleic acid samples from healthy subjects in a reference group of healthy subjects can be analyzed for regions of low variability. Accordingly, each sequence read in the first set of sequence reads of nucleic acid samples from each healthy subject can be aligned to a region in the reference genome. From this, a training set of sequence reads from sequence reads of nucleic acid samples from subjects in a training group can be selected. Each sequence read in the training set can align to a region in the regions of low variability in the reference genome identified from the reference set. The training set can include sequence reads of nucleic acid samples from healthy subjects as well as sequence reads of nucleic acid samples from diseased subjects who are known to have the cancer. The nucleic acid samples from the training group can be of a type that is the same as or similar to that of the nucleic acid samples from the reference group of healthy subjects. From this it can be determined, using quantities derived from sequence reads of the training set, one or more parameters that reflect differences between sequence reads of nucleic acid samples from the healthy subjects and sequence reads of nucleic acid samples from the diseased subjects within the training group. Then, a test set of sequence reads associated with nucleic acid samples comprising cfNA fragments from a test subject whose status with respect to the cancer is unknown can be received, and the likelihood of the test subject having the cancer can be determined based on the one or more parameters.

The M score classifier is described in U.S. Patent Application No. 62/642,480, entitled "Methylation Fragment Anomaly Detection," filed Mar. 13, 2018, which is hereby incorporated by reference.

Ensembles of classifiers and boosting. In some embodiments, an ensemble (two or more) of classifiers is used. In some embodiments, a boosting technique such as AdaBoost is used in conjunction with many other types of learning algorithms to improve the performance of the classifier. In this approach, the output of any of the classifiers disclosed herein, or their equivalents, is combined into a weighted sum that represents the final output of the boosted classifier.

Example 3—Cell-Free Genome Atlas Study (CCGA) Cohorts

Subjects from the CCGA [NCT02889978] were used in the Examples of the present disclosure. CCGA is a prospective, multi-center, observational cfDNA-based early cancer detection study that has enrolled 15,254 demographically-balanced participants at 141 sites. Blood samples were collected from the 15,254 enrolled participants (56% cancer, 44% non-cancer) from subjects with newly diagnosed therapy-naive cancer (C, case) and participants without a diagnosis of cancer (noncancer [NC], control) as defined at enrollment.

In a first cohort (pre-specified substudy) (CCGA-1), plasma cfDNA extractions were obtained from 3,583 CCGA and STRIVE participants (CCGA: 1,530 cancer subjects and 884 non-cancer subjects; STRIVE 1,169 non-cancer participants). STRIVE is a multi-center, prospective, cohort study enrolling women undergoing screening mammography (99, 259 participants enrolled). Blood was collected (n=1,785) from 984 CCGA participants with newly diagnosed, untreated cancer (20 tumor types, all stages) and 749 participants with no cancer diagnosis (controls) for plasma cfDNA extraction. This preplanned substudy included 878 cases, 580 controls, and 169 assay controls (n=1627) across twenty tumor types and all clinical stages.

Three sequencing assays were performed on the blood drawn from each participant: 1) paired cfDNA and white blood cell (WBC)-targeted sequencing (60,000×, 507 gene panel) for single nucleotide variants/indels (the ART sequencing assay); a joint caller removed WBC-derived somatic variants and residual technical noise; 2) paired cfDNA and WBC whole-genome sequencing (WGS; 35×) for copy number variation; a novel machine learning algorithm generated cancer-related signal scores; joint analysis identified shared events; and 3) cfDNA whole-genome bisulfite sequencing (WGBS; 34×) for methylation; normalized scores were generated using abnormally methylated fragments. In addition, tissue samples were obtained from participants with cancer only, such that 4) whole-genome sequencing (WGS; 30×) was performed on paired tumor and WBC gDNA for identification of tumor variants for comparison.

Within the context of the CCGA-1 study, several methods were developed for estimating tumor fraction of a cfDNA sample (see e.g., U.S. Pat. Appl. 62/658,479 filed on Apr. 16, 2018 entitled "Systems and Methods for Determining Tumor Fraction in Cell-Free Nucleic Acid"; U.S. Pat. Appl. 62/834,904 filed on Apr. 16, 2019 entitled "Systems and Methods for Tumor Fraction Estimation from Small Variants"; and U.S. Pat. Appl. 62/781,549 filed on Dec. 18, 2018 entitled "Systems and Methods for Estimating Cell Source Fractions Using Methylation Information," which are each herein incorporated in their entirety). For example, one of the approaches was illustrated as method 700 in FIG. 7A. In this approach, nucleic acid samples from formalin-fixed, paraffin-embedded (FFPE) tumor tissues (e.g., 704) and nucleic acid samples from white blood cells (WBC) from the matching patient (e.g., 706) were sequenced by whole-genome sequencing (WGS). Somatic variants identified based on the sequencing data (e.g., 708) were analyzed against matching cfDNA sequencing data from the same patient (e.g., 710) were used to determine a tumor fraction estimate (e.g., 712).

In a second pre-specified substudy (CCGA-2), a targeted, rather than whole-genome, bisulfite sequencing assay was used to develop a classifier of cancer versus non-cancer and tissue-of-origin based on a targeted methylation sequencing approach. For Approach 2, 3,133 training participants and 1,354 validation samples (775 having cancer; 579 not having cancer as determined at enrollment, prior to confirmation of cancer versus non-cancer status) were used. Plasma cfDNA was subjected to a bisulfite sequencing assay (the COMPASS assay) targeting the most informative regions of the methylome, as identified from a unique methylation database and prior prototype whole-genome and targeted sequencing assays, to identify cancer and tissue-defining methylation signal. Of the original 3,133 samples reserved for training, only 1,308 samples were deemed clinically evaluable and analyzable. Analysis was performed on a primary analysis population n=927 (654 cancer and 273 non-cancer) and a secondary analysis population n=1,027 (659 cancer and 373 non-cancer). Finally, genomic DNA from formalin-fixed, paraffin-embedded (FFPE) tumor tissues and isolated cells from tumors was subjected to whole-genome bisulfite sequencing (WGBS) to generate a large database of cancer-defining methylation signals for use in panel design and in training to optimize performance.

These data demonstrate the feasibility of achieving >99% specificity for invasive cancer, and support the promise of cfDNA assay for early cancer detection. See, e.g., Klein et al., 2018, "Development of a comprehensive cell-free DNA (cfDNA) assay for early detection of multiple tumor types: The Circulating Cell-free Genome Atlas (CCGA) study," J. Clin. Oncology 36(15), 12021-12021; doi: 10.1200/JCO.2018.36.15_suppl.12021, and Liu et al., 2019, "Genome-wide cell-free DNA (cfDNA) methylation signatures and effect on tissue of origin (TOO) performance," J. Clin. Oncology 37(15), 3049-3049; doi: 10.1200/JCO.2019.37.15_suppl.3049, each of which is hereby incorporated herein by reference in its entirety.

Within the context of the CCGA-2 study, multiple methods were developed for estimating tumor fraction of a cfDNA sample based on methylation data (obtained by targeted methylation or WGBS) (See e.g., U.S. Pat. Appl. 62/781,549 filed on Dec. 18, 2018 entitled "Systems and Methods for Estimating Cell Source Fractions Using Methylation Information," and U.S. Pat. Appl. 62/983,443 filed on Feb. 28, 2020 entitled "Identifying Methylation Patterns that Discriminate or Indicate A Cancer Condition," which are each herein incorporated in their entirety). For example, one of the approaches was illustrated as method 702 in FIG. 7B see e.g., U.S. Pat. Appl. 62/972,375 filed on Feb. 10, 2020, entitled "Systems and Methods for Tumor Fraction Estimation from Small Variants," which is hereby incorporated in its entirety). In this approach, nucleic acid samples from formalin-fixed, paraffin-embedded (FFPE) tumor tissues (e.g., 714) were analyzed by whole-genome bisulfite sequencing (WGBS). Somatic variants identified based on the sequencing data (e.g., 716) were analyzed against matching cfDNA WGBS sequencing data from the same patient (e.g., 718) were used to determine a tumor fraction estimate (e.g., 720). An example of tumor fraction analysis based on WGBS sequencing data can be found in Example 7.

Example 4—Tumor Fraction Estimation

Figures 7A, 7B:
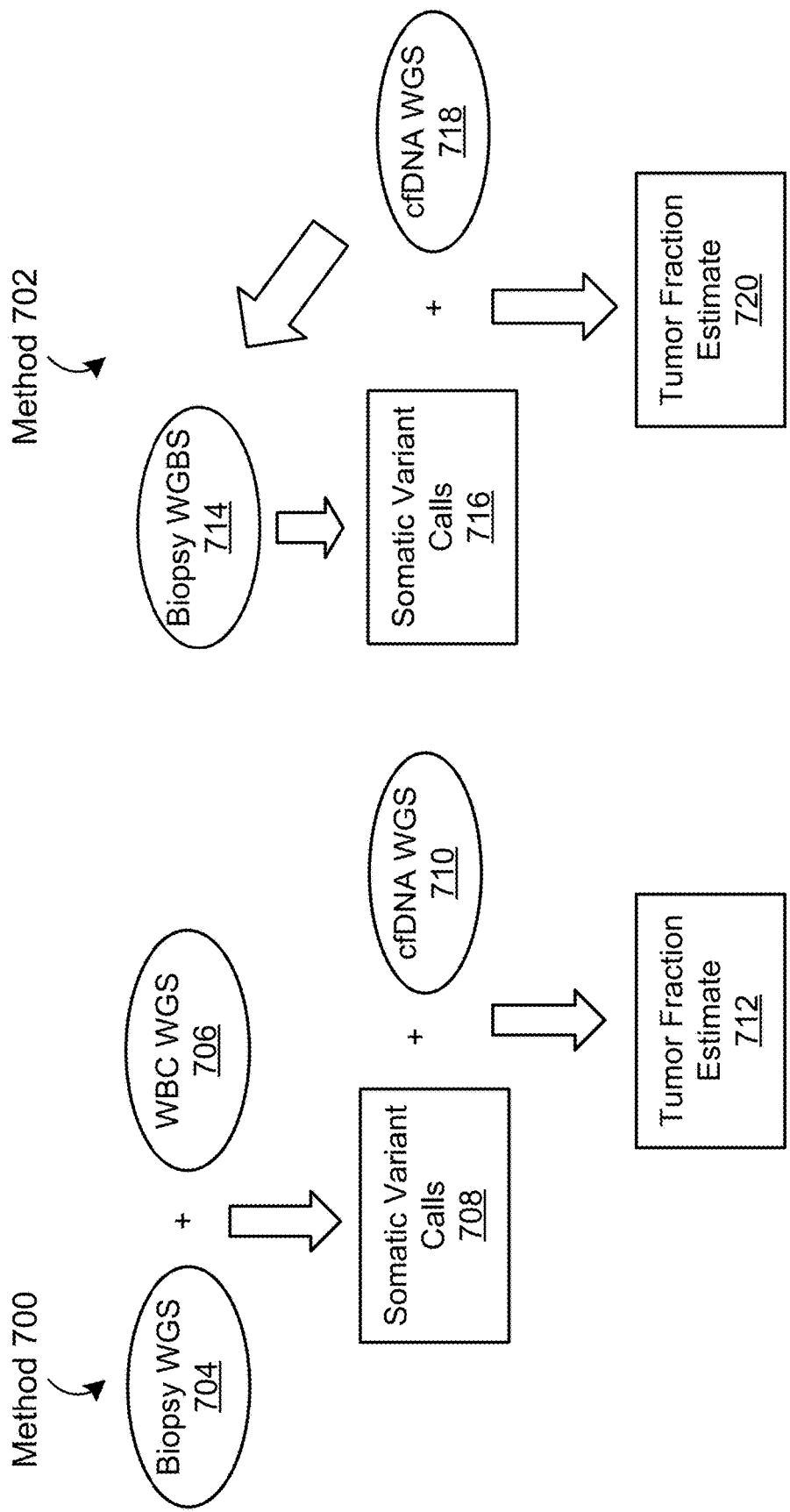
FIGS. 7A and 7B illustrate two examples of tumor fraction estimation (e.g., 700 and 702) that can be performed in accordance with some embodiments of the present disclosure.

FIGS. 7A and 7B illustrate two examples of tumor fraction estimation (e.g., 700 and 702) that can be performed in accordance with some embodiments of the present disclosure. In particular, method 700 in FIG. 7A comprises the use of whole-genome sequencing of a biopsy 704 and matched white blood cell whole genome sequencing 706 to determine a set of potentially informative somatic variant calls (e.g., 708). Germline variants are typically not involved with the development of cancer and as such typically provide less information than somatic variants in terms of detecting and/or identifying cancer. Method 700, in some embodiments, continues by obtaining 710 whole-genome sequencing information of cell-free DNA of a test subject. The combination of known somatic variant calls 708 as the search space and subject-specific variants 710 then can be used to provide a tumor fraction estimate 712 for the subject. Method 702 in FIG. 7B, in contrast, does not incorporate information from white blood cell sequencing. Instead, method 702 uses information from biopsy whole-genome bisulfite sequencing 714 to generate a set of somatic variant calls 716. In some embodiments, the 716 set of somatic variants differs from the 708 set of somatic variants determined in method 700. Method 702, in some embodiments, proceeds by obtaining 718 whole-genome sequencing of cell-free DNA for a test subject. The combination of known somatic variant calls 716 as the search space and subject-specific variants from the cell-free DNA sequencing 718 can then be used to provide a tumor fraction estimate 712 for the subject. In some embodiments, for methods 700 and 702, steps 704, 706, and 714 are performed for a set of training subjects. In some embodiments of methods 700 and 702, one or more of the steps 704, 706, or 714 are performed on the respective test subject.

CONCLUSION

The terminology used herein is for the purpose of describing particular cases and is not intended to be limiting. As used herein, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation (s).

It will also be understood that, although the terms first, second, etc. may be used herein to describe various elements, these elements should not be limited by these terms. These terms are used to distinguish one element from another. For example, a first subject could be termed a second subject, and, similarly, a second subject could be termed a first subject, without departing from the scope of the present disclosure. The first subject and the second subject are both subjects, but they are not the same subject.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event)" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed:

1. A method of determining a contamination status of a test biological sample obtained from a test subject, comprising:
   (a) obtaining, in electronic format, one or more training subject datasets, each training subject dataset comprising a corresponding training variant allele frequency of each respective training single nucleotide variant in a plurality of training single nucleotide variants;
   (b) training a computational neural network based on the one or more training subject datasets, wherein the computational neural network comprises a pre-trained convolutional neural network and an untrained classifier;
   (c) obtaining, in electronic format, a test subject dataset comprising a corresponding test variant allele frequency of each respective test single nucleotide variant in a plurality of test single nucleotide variants; and
   (d) determining the contamination status for the test biological sample based on the trained computational neural network and the test subject dataset.

2. The method of claim 1, wherein the corresponding training variant allele frequency is determined by sequencing of one or more nucleic acids in a respective training biological sample obtained from a respective training subject.

3. The method of claim 2, wherein the respective training biological sample is substantially cell-free sample of blood plasma or blood serum obtained from the respective training subject.

4. The method of claim 1, wherein the corresponding training variant allele frequency is between 0 and 1.

5. The method of claim 1, wherein the training dataset subject dataset further comprises one or more contamination indications.

6. The method of claim 5, wherein each of the one or more contamination indications is at least 0%, 0.1%, 0.3%, 0.5%, 1%, 5%, 10%, 15%, 20%, or 25%.

7. The method of claim 5, wherein the training comprises constructing one or more channels comprising one or more parameters, wherein the one or more parameters comprise at least one parameter associated with the one or more contamination indications.

8. The method of claim 1, wherein the training comprises constructing one or more channels comprising one or more parameters, wherein the one or more parameters comprise at least one parameter associated with the corresponding variant allele frequency.

9. The method of claim 1, wherein the plurality of training single nucleotide variants comprises 100 or more single nucleotide variants, 200 or more single nucleotide variants, 500 or more single nucleotide variants, 1000 or more single nucleotide variants, 2000 or more single nucleotide variants, 2000 or more single nucleotide variants, 4000 or more single nucleotide variants, or 10000 or more single nucleotide variants.

10. The method of claim 1, wherein the pre-trained convolutional neural network comprises LeNet, AlexNet, VGGNet 16, GoogLeNet, or ResNet.

11. The method of claim 1, wherein the corresponding test variant allele frequency is determined by sequencing of one or more nucleic acids in the test biological sample obtained from the test subject.

12. The method of claim 1, wherein the test biological sample is substantially cell-free sample of blood plasma or blood serum obtained from the test subject.

13. The method of claim 1, wherein the contamination status comprises an estimation of contamination percentage for the test biological sample of the test subject.

14. A system for determining a contamination status of a test biological sample obtained from a test subject:
   a storage device that stores instructions; and
   at least one processor that executes the instructions in order for:
   (a) obtaining, in electronic format, one or more training subject datasets, each training subject dataset comprising a corresponding training variant allele frequency of each respective training single nucleotide variant in a plurality of training single nucleotide variants;
   (b) training a computational neural network based on the one or more training subject datasets, wherein the computational neural network comprises a pre-trained convolutional neural network and an untrained classifier;
   (c) obtaining, in electronic format, a test subject dataset comprising a corresponding test variant allele frequency of each respective test single nucleotide variant in a plurality of test single nucleotide variants; and
   (d) determining the contamination status for the test biological sample based on the trained computational neural network and the test subject dataset.

15. The system of claim 14, wherein the corresponding training variant allele frequency is determined by sequencing of one or more nucleic acids in a respective training biological sample obtained from a respective training subject.

16. The system of claim 15, wherein the respective training biological sample is substantially cell-free sample of blood plasma or blood serum obtained from the respective training subject.

17. The system of claim 14, wherein the corresponding training variant allele frequency is between 0 and 1.

18. The system of claim 14, wherein the training dataset subject dataset further comprises one or more contamination indications.

19. The system of claim 18, wherein each of the one or more contamination indications is at least 0%, 0.1%, 0.3%, 0.5%, 1%, 5%, 10%, 15%, 20%, or 25%.

20. A non-transitory computer-readable medium storing instructions for determining a contamination status of a test biological sample obtained from a test subject comprising:
   (a) obtaining, in electronic format, one or more training subject datasets, each training subject dataset comprising a corresponding training variant allele frequency of each respective training single nucleotide variant in a plurality of training single nucleotide variants;
   (b) training a computational neural network based on the one or more training subject datasets, wherein the computational neural network comprises a pre-trained convolutional neural network and an untrained classifier;
   (c) obtaining, in electronic format, a test subject dataset comprising a corresponding test variant allele frequency of each respective test single nucleotide variant in a plurality of test single nucleotide variants; and
   (d) determining the contamination status for the test biological sample based on the trained computational neural network and the test subject dataset.

* * * * *